United States Patent
Pfaendner et al.

(10) Patent No.: US 10,913,743 B2
(45) Date of Patent: Feb. 9, 2021

(54) USE OF ORGANIC OXYIMIDES AS FLAME RETARDANT FOR PLASTIC MATERIALS AND ALSO FLAME-RETARDANT PLASTIC MATERIAL COMPOSITION AND MOULDED PARTS PRODUCED THEREFROM

(71) Applicant: FRAUNHOFER-GESELLSCHAFT ZUR FÖRDERUNG DER ANGEWANDTEN FORSCHUNG E.V., Munich (DE)

(72) Inventors: Rudolf Pfaendner, Rimbach (DE); Elke Metzsch-Zilligen, Steffeln (DE); Maria Stec, Darmstadt (DE)

(73) Assignee: Fraunhofer-Gesellschaft zur förderung der angewandten Forschung e.V., München (DE)

( * ) Notice: Subject to any disclaimer, the term of this patent is extended or adjusted under 35 U.S.C. 154(b) by 0 days.

(21) Appl. No.: 14/779,849

(22) PCT Filed: Mar. 24, 2014

(86) PCT No.: PCT/EP2014/055847
§ 371 (c)(1),
(2) Date: Sep. 24, 2015

(87) PCT Pub. No.: WO2014/154636
PCT Pub. Date: Oct. 2, 2014

(65) Prior Publication Data
US 2016/0052927 A1    Feb. 25, 2016

(30) Foreign Application Priority Data

Mar. 25, 2013  (DE) .......................... 10 2013 005 307

(51) Int. Cl.
| | |
|---|---|
| C07D 487/04 | (2006.01) |
| C08K 5/3417 | (2006.01) |
| C09K 21/10 | (2006.01) |
| C08K 5/00 | (2006.01) |
| C08K 5/32 | (2006.01) |
| C07D 207/46 | (2006.01) |
| C07D 209/48 | (2006.01) |
| C07D 221/14 | (2006.01) |
| C09D 123/12 | (2006.01) |
| C08K 5/5313 | (2006.01) |

(52) U.S. Cl.
CPC ......... *C07D 487/04* (2013.01); *C07D 207/46* (2013.01); *C07D 209/48* (2013.01); *C07D 221/14* (2013.01); *C08K 5/0066* (2013.01); *C08K 5/32* (2013.01); *C08K 5/3417* (2013.01); *C09D 123/12* (2013.01); *C09K 21/10* (2013.01); *C08K 5/5313* (2013.01)

(58) Field of Classification Search
None
See application file for complete search history.

(56) References Cited

U.S. PATENT DOCUMENTS

| | | |
|---|---|---|
| 2,682,522 A | 6/1954 | Coover et al. |
| 2,716,101 A | 8/1955 | Coover et al. |
| 2,891,915 A | 6/1959 | McCormack et al. |
| 3,326,852 A | 6/1967 | Thomas |
| 3,442,854 A | 5/1969 | Curtius et al. |
| 3,488,329 A | 1/1970 | Johnson |
| 3,578,641 A | 5/1971 | Johnson |
| 3,915,930 A | 10/1975 | Dotson, Jr. et al. |
| 3,919,363 A | 11/1975 | Ura et al. |
| 3,946,093 A | 3/1976 | Koto et al. |
| 4,218,332 A | 8/1980 | Schwab et al. |
| 4,328,174 A | 5/1982 | Schmidt et al. |
| 4,331,614 A | 5/1982 | Schmidt et al. |
| 4,374,971 A | 2/1983 | Schmidt et al. |
| 4,415,719 A | 11/1983 | Schmidt et al. |
| 5,216,113 A | 6/1993 | Schulz-Schlitte et al. |
| 5,334,692 A | 8/1994 | Hess et al. |
| 6,288,210 B1 | 9/2001 | Shobha et al. |
| 6,291,630 B1 | 9/2001 | König et al. |
| 6,861,499 B2 | 3/2005 | Vinciguerra et al. |
| 7,115,765 B2 | 10/2006 | Sprenger et al. |
| 7,390,970 B2 | 6/2008 | Lee et al. |
| 7,745,519 B2 | 6/2010 | Ihara et al. |
| 7,816,486 B2 | 10/2010 | Freitag et al. |

(Continued)

FOREIGN PATENT DOCUMENTS

| | | |
|---|---|---|
| CA | 819181 A | 7/1969 |
| CN | 101258194 A | 9/2008 |

(Continued)

OTHER PUBLICATIONS

Imajo et al., "Polymides derived from bis-N-hydroxyimides. III. Polymide-carbonates and polymide-urethanes synthesized from bischlorformate of N,N'-dihydroxypyromellitic diimide," *Journal of Polymer Science Part A: Polymer Chemistry*, vol. 19(7), pp. 1855-1861 (1981).

Spatz et al. "Some N-Substituted Tetrabromophthalimide Fire-Retardant Additives", *Industrial & Engineering Chemistry Product Research and Development*, vol. 8, pp. 397-398 (1969).

Wilén et al., "Improving weathering resistance of flame-retarded polymers," *Journal of Applied Polymer Science* 129(3):925-944 (2013).

European Patent Office, International Search Report in International Application No. PCT/EP2014/055847 (dated Jun. 12, 2014).

(Continued)

*Primary Examiner* — Robert T Butcher
(74) *Attorney, Agent, or Firm* — Leydig, Voit & Mayer, Ltd.

(57) ABSTRACT

The present invention relates to the use of organic oxy imides as flame retardants for plastics. According to the present invention, a flame-retardant plastics composition is likewise specified, including an oxy imide as flame retardant. Additionally specified are mouldings produced from an inventive flame-retardant polymer composition.

12 Claims, No Drawings

(56) References Cited

U.S. PATENT DOCUMENTS

| | | | |
|---|---|---|---|
| 7,872,198 | B2 | 1/2011 | Lee et al. |
| 8,058,329 | B2 | 11/2011 | Just et al. |
| 8,288,456 | B2 | 10/2012 | Feldermann et al. |
| 8,349,925 | B2 | 1/2013 | Butz |
| 8,853,307 | B2 | 10/2014 | Butz |
| 10,138,354 | B2 | 11/2018 | Pfaendner et al. |
| 2005/0020800 | A1 | 1/2005 | Levchik et al. |
| 2005/0064177 | A1 | 3/2005 | Lee et al. |
| 2005/0176983 | A1 | 8/2005 | Sprenger et al. |
| 2007/0135538 | A1 | 6/2007 | Ihara et al. |
| 2007/0197697 | A1 | 8/2007 | Botkin et al. |
| 2007/0219295 | A1 | 9/2007 | Levchik et al. |
| 2008/0045673 | A1 | 2/2008 | Piotrowski et al. |
| 2008/0167405 | A1 | 7/2008 | Just et al. |
| 2008/0226918 | A1 | 9/2008 | Lee et al. |
| 2009/0118394 | A1 | 5/2009 | Feldermann et al. |
| 2009/0286060 | A1 | 11/2009 | Sala et al. |
| 2010/0230158 | A1 | 9/2010 | Hase et al. |
| 2010/0280215 | A1 | 11/2010 | Just et al. |
| 2011/0027512 | A1 | 2/2011 | Lee et al. |
| 2011/0256457 | A1* | 10/2011 | Utsumi ............... C07C 239/22 429/336 |
| 2011/0257310 | A1 | 10/2011 | Butz |
| 2013/0203928 | A1 | 8/2013 | Hocke et al. |
| 2014/0005289 | A1 | 1/2014 | Butz |
| 2016/0052927 | A1 | 2/2016 | Pfaendner et al. |
| 2016/0272789 | A1 | 9/2016 | Pfaendner et al. |
| 2017/0107375 | A1 | 4/2017 | Pfaendner et al. |
| 2017/0121499 | A1 | 5/2017 | Pfaendner et al. |
| 2017/0260362 | A1 | 9/2017 | Pfaendner et al. |
| 2017/0260363 | A1 | 9/2017 | Pfaendner et al. |
| 2017/0260366 | A1 | 9/2017 | Pfaendner et al. |
| 2017/0267835 | A1 | 9/2017 | Groos et al. |
| 2018/0186970 | A1 | 7/2018 | Groos et al. |

FOREIGN PATENT DOCUMENTS

| | | |
|---|---|---|
| CN | 102031101 | 4/2011 |
| CN | 102115530 A | 7/2011 |
| CN | 102115558 A | 7/2011 |
| CN | 102222798 A | 10/2011 |
| CN | 102250400 A | 11/2011 |
| CN | 102342869 A | 2/2012 |
| CN | 102344598 A | 2/2012 |
| CN | 102382453 A | 3/2012 |
| CN | 102585429 A | 7/2012 |
| DE | 268 249 A1 | 5/1989 |
| DE | 100 22 946 A1 | 11/2001 |
| DE | 600 07 914 T2 | 12/2004 |
| DE | 10 2004 010 455 A1 | 9/2005 |
| DE | 10 2007 040927 A1 | 3/2009 |
| DE | 11 2008 003 070 T5 | 9/2010 |
| DE | 10 2009 047030 A1 | 2/2011 |
| DE | 10 2013 005 307 A1 | 9/2014 |
| EP | 0 303 988 A2 | 2/1989 |
| EP | 0 767 182 A2 | 4/1997 |
| EP | 0 935 619 B1 | 6/2001 |
| EP | 2 426 163 A1 | 3/2012 |
| EP | 2 450 401 A1 | 5/2012 |
| JP | S54-149751 A | 11/1979 |
| JP | H03-41188 A | 2/1991 |
| JP | H10-213912 A | 8/1998 |
| JP | 2005-344113 A | 12/2005 |
| JP | 2006-299091 A | 11/2006 |
| JP | 2007-016162 A | 1/2007 |
| JP | 2007-016163 A | 1/2007 |
| JP | 2009-507116 A | 2/2009 |
| JP | 2009-102621 A | 5/2009 |
| JP | 2009-242969 A | 10/2009 |
| JP | 2013-512977 A | 4/2013 |
| JP | 2013-531084 A | 8/2013 |
| WO | WO 1999/00450 A1 | 1/1999 |
| WO | WO 2002/074847 A1 | 9/2002 |
| WO | WO 2003/016388 A1 | 2/2003 |
| WO | WO 2003/070736 A1 | 8/2003 |
| WO | WO 2006/084488 A1 | 8/2006 |
| WO | WO 2006/084489 A1 | 8/2006 |
| WO | WO 2008/101845 A1 | 8/2008 |
| WO | WO 2009/080554 A1 | 7/2009 |
| WO | WO 2010/026230 A1 | 3/2010 |
| WO | WO 2010/135398 A1 | 11/2010 |
| WO | WO 2011/000019 A1 | 1/2011 |
| WO | WO 2011/003773 A1 | 1/2011 |
| WO | WO 2011/086114 A1 | 7/2011 |
| WO | WO 2011/117266 A1 | 9/2011 |
| WO | WO 2011/156077 A1 | 12/2011 |
| WO | WO 2012/052376 A1 | 4/2012 |
| WO | WO 2012/089998 A2 | 7/2012 |
| WO | WO 2013/020696 A2 | 2/2013 |
| WO | WO 2013/068437 A2 | 5/2013 |
| WO | WO 2013/072295 A1 | 5/2013 |
| WO | WO 2014/076273 A1 | 5/2014 |
| WO | WO 2015/180888 A1 | 12/2015 |
| WO | WO 2015/189034 A1 | 12/2015 |

OTHER PUBLICATIONS

European Patent Office, Written Opinion in International Application No. PCT/EP2014/055847 (dated Jun. 12, 2014).
International Bureau of WIPO, International Preliminary Report on Patentability in International Application No. PCT/EP2014/055847 (dated Sep. 29, 2015).
Imajo et al., "Polyimides derived from bis-N-hydroxyimides. II. Synthesis and properties of polyimide-esters," *Journal of Polymer Science Part A: Polymer Chemistry*, vol. 18(7), pp. 2189-2196 (1980).
Pfaendner, "Nitroxyl radicals and nitroxylethers beyond stabilization: radical generators for efficient polymer modification," *Comptes Rendus Chimie* 9(11):1338-1344 (2006).
Japanese Patent Office, Notice of Rejection issued in Japanese Application No. 2016-503685 (dated Jan. 30, 2017).
Aubert et al., "Azoalkanes—novel flame retardants and their structure—property relationship," *Polym. Adv. Technol.* 22(11): 1529-1538 (2011).
Carpino et al.. "The uronium/guanidinium peptide coupling reagents: Finally the true uronium salts," *Angewandte Chemie-International Edition* 41: 442-445 (2002).
Dintcheva et al., "Photo-oxidation behaviour of polyethylene/multi-wall carbon nanotube composite films," *Polymer Degradation and Stability*, vol. 94, No. 2, pp. 162-170 (2008).
Katsenis et al., "Initial use of 1-hydroxybenzotriazole in the chemistry of group 12 metals: An 1D zinc(II) coordination polymer and a mononuclear cadmium(II) complex containing the deprotonated ligand in a novel monodentate ligation mode," *Inorg. Chem. Comm.* 12(2): 92-96 (2009).
Pawelec et al., "Triazene compounds as a novel and effective class of flame retardants for polypropylene," *Polym. Degrad. Stab.* 87(6): 48-954 (2012).
*Plastics Additives Handbook*, 5th edition, Chapter I —"Antioxidants," H. Zweifel, editor, Munich, pp. 1-139 (2001).
Shi et al., "Influence of wall Number and surface functionalization of carbon nanotubes on their antioxidant behavior in high density polyethylene," *Carbon*, 50(3):1005-1013 (2012).
Spitalsky et al., "Carbon nanotube-polymer composites: Chemistry, processing, mechanical and electrical properties," *Progr. Pol. Sci.* 35:357-401 (2010).
Watts et al., "Carbon nanotubes as polymer antioxidants," *J. Mater. Chem.*, 3(13): 491-495 (2003).
Zeynalov et al., "Antioxidative Activity of Carbon Nanotube and Nanofiber," *The Open Materials Science Journal*, vol. 2, pp. 28-34 (2008).
Korean Intellectual Property Office, Office Action issued in Korean Application No. 10-2015-7027558 (dated Apr. 27, 2017) 11 pp.
State Intellectual Property Office of People's Republic of China, Second Office Action issued in Chinese Application No. 201480017757.X (dated Dec. 25, 2017).
State Intellectual Property Office of People's Republic of China, Search Report issued in Chinese Application No. 201480017757X (dated Mar. 25, 2017) 5 pp.

(56) References Cited

OTHER PUBLICATIONS

State Intellectual Property Office of People's Republic of China, Office Action issued in Chinese Application No. 201480017757X (dated Apr. 1, 2017) 17 pp.
Korean Patent Office, Notification of Reason for Refusal in Korean Patent Application No. 10-2018-7016819 (dated Dec. 12, 2018).
Habicher et al., "Organic Phosphites as Polymer Stabilizers", *Macromol. Symp.* 225: 147-164 (2005).

* cited by examiner

USE OF ORGANIC OXYIMIDES AS FLAME RETARDANT FOR PLASTIC MATERIALS AND ALSO FLAME-RETARDANT PLASTIC MATERIAL COMPOSITION AND MOULDED PARTS PRODUCED THEREFROM

CROSS-REFERENCE TO RELATED APPLICATIONS

This patent application is the U.S. national phase of International Application No. PCT/EP2014/055847, filed on Mar. 24, 2014, which claims the benefit of German Patent Application No. 10 2013 005 307.2, filed Mar. 25, 2013, the disclosures of which are incorporated herein by reference in their entireties for all purposes.

The present invention relates to the use of organic oxyimides as flame retardant for plastic materials. According to the present invention, a flame-retardant plastic material composition is likewise indicated, which includes an oxyimide as flame retardant. In addition, moulded parts, produced from a flame-retardant polymer composition according to the invention, are indicated.

Most plastic materials, such as e.g. plastic materials based on polyolefins, polystyrene, polyamides, polyurethanes or polyesters, are combustible and comparatively easily inflammable. In order to reduce or exclude the risk of fire of plastic materials in specific applications, it is therefore absolutely necessary to reduce the flammability and to use flameproof or flame-retardant plastic material compositions. For this purpose, generally flame retardants are added to the plastic material with the aim of preventing ignition for a specific time or significantly reducing the spread of fire. Traditional flame retardants are based on chlorine- and bromine-containing compounds (generally in combination with antimony trioxide), on phosphorus-containing, on nitrogen-containing compounds and/or on inorganic hydroxides. In modern times, halogen-free flame-retardant solutions are preferred for environmental reasons and/or from the point of view of toxicology.

For the production of flame-retardant plastic materials, there is a large number of flame retardants which are used generally specifically for substrates for a specific polymer and a specific field of use, corresponding to the standards which form the basis thereof. Flame-retardant plastic materials are used for example in electrical and electronic applications, in the transport/automobile field and in construction. A very effective flame-retardant class, developed in the last few years, on a nitrogen basis, preferably for polyolefins, is based on alkoxyamines (WO 99/00450, WO 2008101845, WO 2011086114). Due to cleavage of the alkoxyamines, radicals are produced in the case of fire, which radicals become involved in the decomposition process of the polymer and hence cause the flame-retardant effect (C. R. Wilen, R. Pfaendner, J. Appl. Pol. Sci. 2013, R. Pfaendner, C. R. Chemistry 9 (2006), 1338-1344). The alkoxyamines can also be used advantageously in synergistic combinations with other flame retardants (WO 02/074847, WO 03/016388, WO 2010026230, WO 2009080554, WO 2011003773, WO 2011117266). Furthermore, it was found that hydroxylamine stabilisers also can effect a synergistic improvement in the effect of bromine-containing, phosphorus-containing and inorganic flame retardants (WO 02/074847).

The previously mentioned flame retardants known from the state of the art do not however fulfil all requirements placed on these nowadays. Thus these must still be used for example in a relatively high concentration with respect to the plastic material composition to be protected, which can lead for example to impairment in the mechanical properties of the plastic material. Further criteria are for example the thermal stability, discolouration, formation of toxic gases in the case of fire, easy availability on an industrial scale inter alia.

It was the object of the present invention to make available new flame retardants and synergistic flame retardant components which are effective in low concentrations and comparatively readily available.

This object is achieved, with respect to the use of organic oxyimides as flame retardant for plastic materials, with respect to a flame-retardant plastic material composition, with respect to a method for the production of this plastic material composition, and also, with respect to a moulded part, a paint or a coating which is producible from a flame-retardant polymer composition, by the features of the invention described herein. Advantageous developments are also described.

According to the invention, the use of organic oxyimides, comprising at least one structural element of the subsequently illustrated formula I

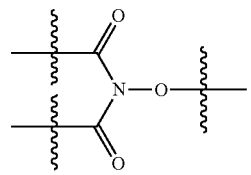

Formula I is indicated as flame retardant for plastic materials.

Formula I should thereby be understood such that the illustrated structural element is contained in the organic oxyimide. The oxyimides used according to the invention should not thereby be equated with isocyanurates or compounds or compound classes derived herefrom. The oxyimide used according to the invention is thereby halogen-free, i.e. the corresponding compound includes no halogen atoms.

It was able to be shown that the organic oxyimides used according to the invention have good effectiveness, as described above, for making plastic materials flame-retardant.

Hence new flame retardants and flame-retardant compositions for polymers are proposed, which, from the point of view of effect and price/performance ratio, represent an attractive alternative to compositions known and used today.

According to a preferred embodiment of the present invention, oxyimides, comprising at least one structural element of the subsequent formula II,

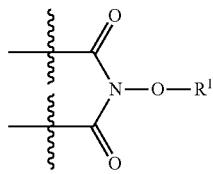

Formula II $R^1$ standing for hydrogen or a possibly substituted alkyl-, cycloalkyl-, aryl-, heteroaryl- or acyl radical, are used as flame retardant.

Alternatively or in combination with the previously mentioned preferred variant, bridged oxyimides, comprising at least one structural element of the subsequent formula III,

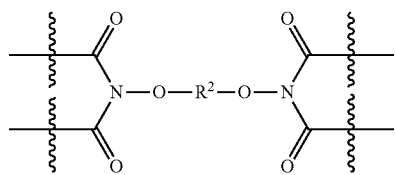

Formula III $R^2$ standing for a possibly substituted akylene-, cycloalkylene-, arylene-, heteroarylene- or bridging acyl radical, can likewise be used.

According to a preferred variant, $R^2$ is selected from radicals of the group consisting of —$(CH_2)_n$— with n=1 to 18, —$CH(CH_3)$—, —$C(CH_3)_2$, —O—, —S—, —$SO_2$—, —NHCO—, —CO— and also the subsequently illustrated groups,

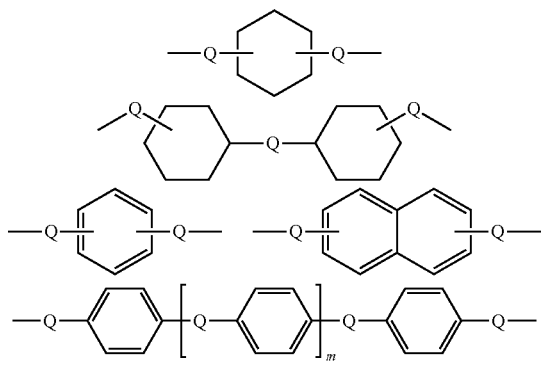

the cycloaliphatic or aromatic ring systems contained in the previously illustrated groups being unsubstituted or substituted by one or more alkyl- and/or alkoxy groups, Q upon each occurrence, being the same or different and being selected from the group consisting of a chemical bond and also the radicals —$(CH_2)_n$— with n=1 to 18, —$CH(CH_3)$—,
—$C(CH_3)_2$—, —O—, —S—, —$SO_2$—,
—NHCO—, —CO—, and m being 0 or 1 to 18.

For particular preference, the radicals $R_2$ are thereby reproduced by the subsequently illustrated structural elements, Q having the above-indicated meaning:

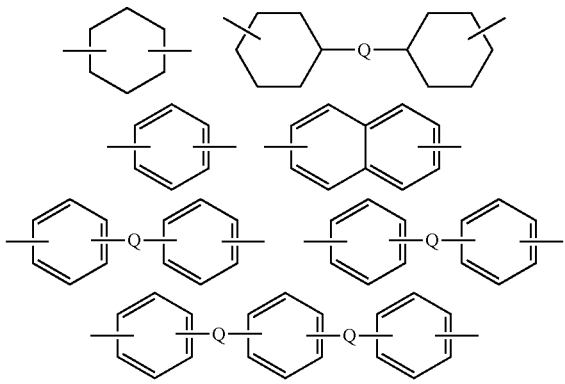

In particular, the radicals $R^2$ can thereby be given by the subsequent structural elements:

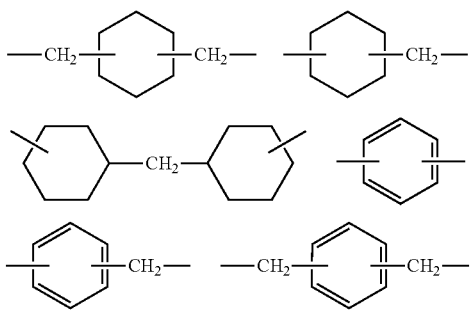

According to a particularly preferred embodiment, the organic oxyimide has one of the subsequent structural formulae:

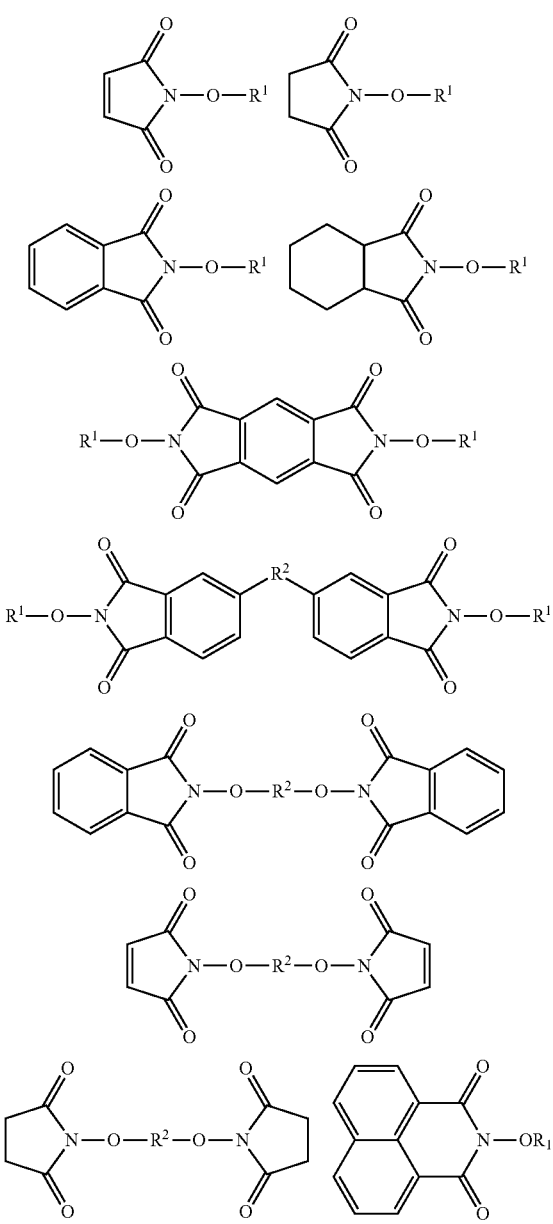

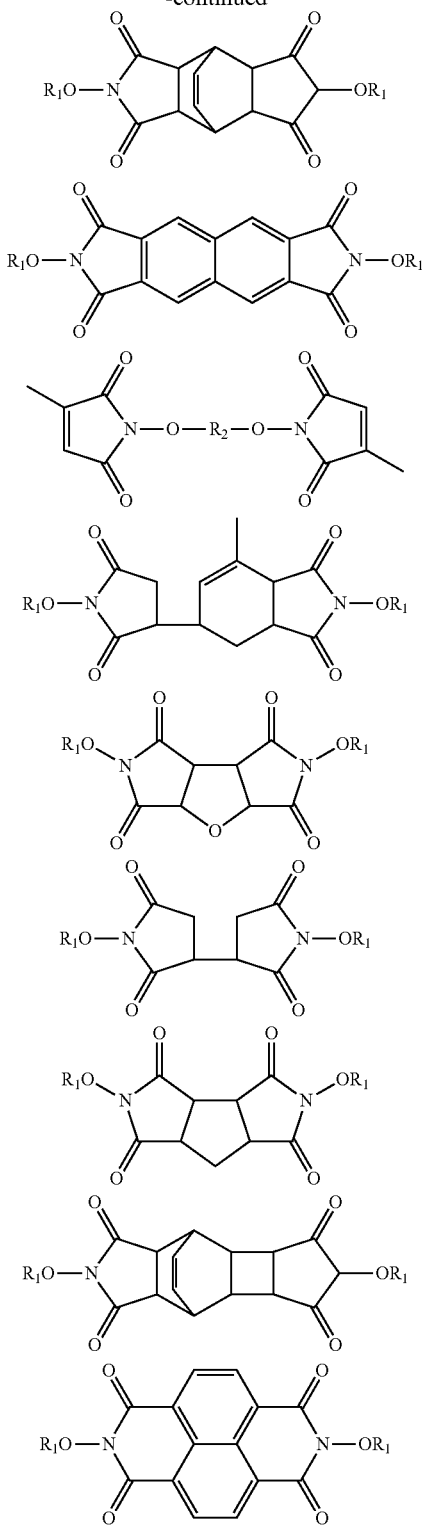

respectively R¹ and R² having the above-indicated meaning.

A particularly preferred radical R¹ is thereby hydrogen or an acyl radical.

The subsequently illustrated compounds with R¹=H are particularly suitable for the purposes of the present invention,

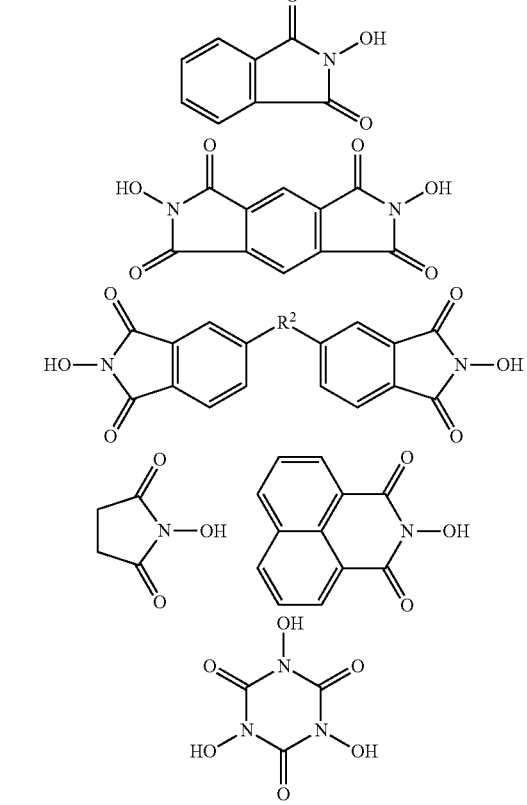

R² having the above-indicated meaning.

Also the subsequently illustrated compounds with R¹=acyl are suitable in particular for the purposes of the present invention.

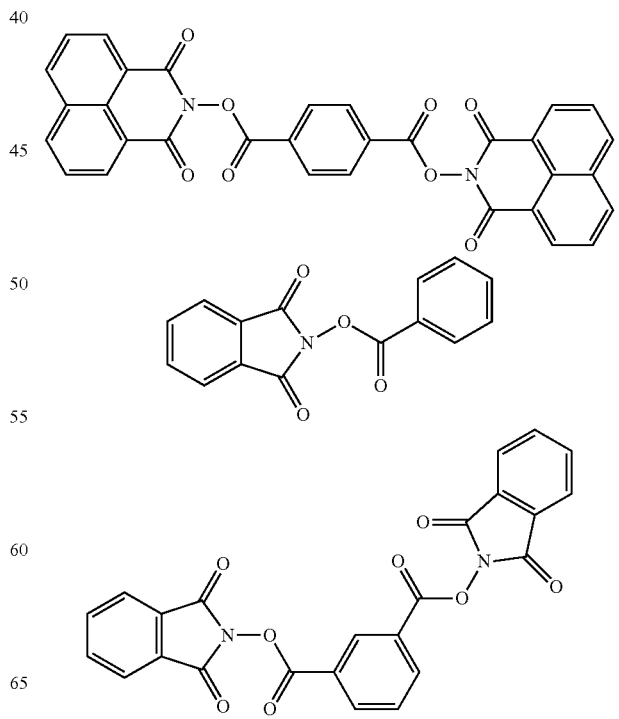

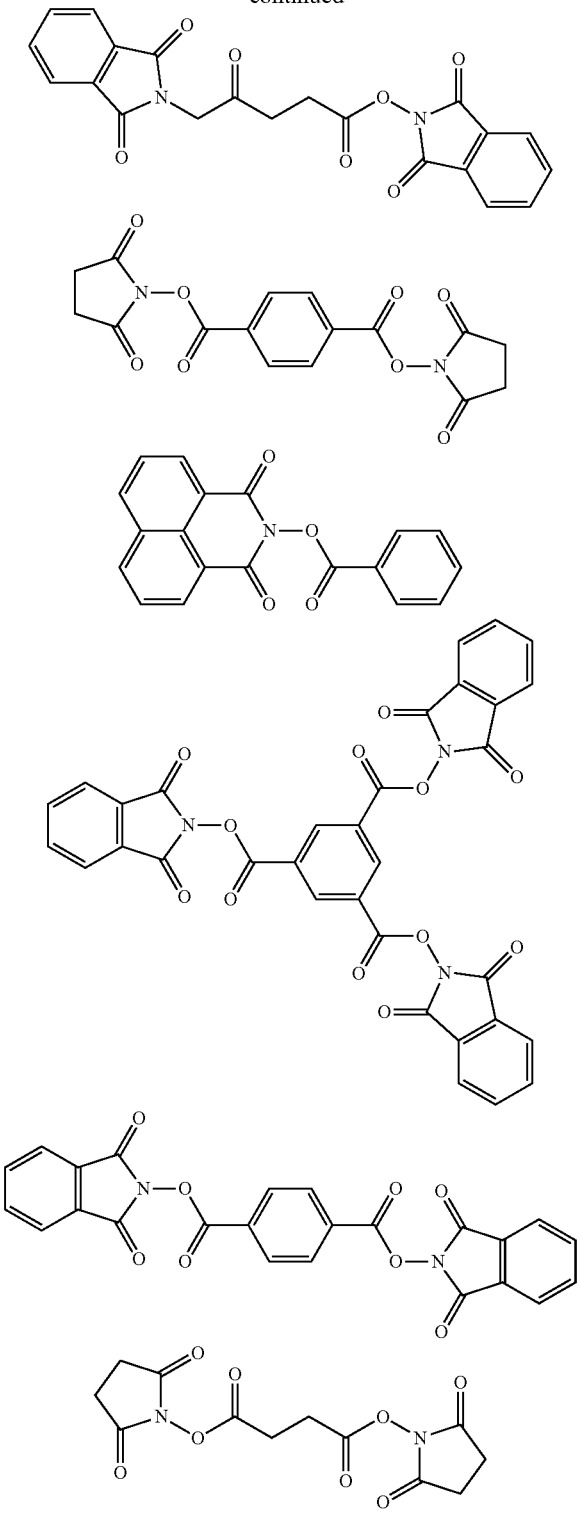

The above-indicated compounds with $R^1$=H are for example available by the reaction of commercially obtainable di- or tetracarboxylic anhydrides with hydroxylamine in the form of the hydrochloride or then with $R^1$=H or $R^2$=acyl by the subsequent esterification of the obtained hydroxylamines with for example an acid chloride or by reesterification from the corresponding acid esters with e.g. readily volatile alcohols, such as e.g. methyl esters.

Furthermore, these hydroxylamine derivatives can also be present in the form of linear oligomers or polymers by, for example, difunctional hydroxylamines ($R^1$=H) being converted, e.g. with difunctional acid chlorides and then the corresponding polyesters being obtained. Analogously, the corresponding linear polyurethanes can be produced from the difunctional hydroxylamines ($R^1$=H) and diisocyanates. The syntheses of these polymers is described in more detail for example in H. Imajo et al., J. Pol. Sci.: Pol. Chem. 18, 2189-2196 (1980) or in H. Imajo et al., J. Pol. Sci.: Pol. Chem. 19, 1855-1861 (1981).

If desired, these polymers can also be synthesised in the form of branched or crosslinked structures by a difunctional component being replaced partially or completely by a tri-, tetra- or higher-functionalised compound, e.g. a trifunctional acid component or a trifunctional hydroxylamine.

Furthermore, it is possible and obvious to the person skilled in the art that copolymers can be synthesised according to the invention by e.g. a difunctional hydroxylimide being replaced partially by a diol compound, such as e.g. ethylene glycol, butanediol-1-4, hexanediol-1,6, hydroquinone, 4,4'-dihydroxybiphenyl. Correspondingly, e.g. copolyesters or copolyurethanes are available. Furthermore, by means of partial exchange of the difunctional hydroxylimides with difunctional compounds structures other than diols such as e.g. diamines, copolymers of mixed structures, such as e.g. polyester amides, are obtainable.

According to the present invention, the organic oxyimides which are used according to the invention can be used for the following illustrated plastic materials, particularly preferred in thermoplastic, elastomeric or duroplastic plastic materials, in particular thermoplastic polymers:

a) polymers made of olefins or diolefins, such as e.g. polyethylene (LDPE, LLDPE, VLDPE, ULDPE, MDPE, HDPE, UHMWPE), metallocene-PE (m-PE), polypropylene, polyisobutylene, poly-4-methylpentene-1, polybutadiene, polyisoprene, polycyclooctene, polyalkylene-carbon monoxide copolymers, and also copolymers in the form of stochastic or block structures such as e.g. polypropylene-polyethylene (EP), EPM or EPDM, ethylene-vinyl acetate (EVA), ethylene-acrylic ester, such as e.g. ethylene-butyl acrylate, ethylene-acrylic acid and the salts thereof (ionomers), and also terpolymers, such as e.g. ethylene-acrylic acid-glycidylacrylate, graft polymers, such as e.g. polypropylene-g-maleic anhydride, polypropylene-g-acrylic acid, polyethylene-g-acrylic acid, b) polystyrene, polymethylstyrene, polyvinylnaphthalene, styrene-butadiene (SB), styrene-butadiene-styrene (SBS), styrene-ethylene-butylene-styrene (SEBS), styene-ethylene-propylene-styrene, styrene-isoprene, styrene-isoprene-styrene (SIS), styrene-butadiene-acrylonitrile (ABS), styrene-acrylonitrile-acrylate (ASA), styrene-ethylene, styrene-maleic anhydride polymers incl. corresponding graft copolymers, such as e.g. styrene on butadiene, maleic anhydride on SBS or SEBS, and also graft copolymers made of methylmethacrylate, styrene-butadiene and ABS (MABS), c) halogen-containing polymers, such as e.g polyvinyl chloride (PVC), polychloroprene and polyvinylidene chloride (PVDC), copolymers made of vinyl chloride and vinylidene chloride or made of vinyl chloride and vinyl acetate, chlorinated polyethylene, polyvinylidene fluoride, d) polymers of unsaturated esters, such as e.g polyacrylates and polymethacrylates, such as polymethylmethacrylate (PMMA), polybutylacrylate, polylaurylacrylate, polystearylacrylate, polyacrylonitrile, polyacrylamides, copolymers, such as e.g. polyacrylonitrile-polyalkylacrylate, e) polymers made of unsaturated alcohols and derivates, such as e.g. polyvinyl alcohol, polyvinyl acetate, polyvinyl butyral, f) polyacetals, such as e.g. polyoxymethylene (POM) or copolymers with e.g. butanal, g) polyphenylene oxides and blends with polystyrene or polyamides, h) polymers of cyclic ethers, such as e.g. polyethylene glycol, polypropylene glycol, polyethylene oxide, polypropylene oxide, i) polyurethanes, made of hydroxy-terminated polyethers or polyesters and aromatic or aliphatic isocyanates, in particular linear polyurethanes, polyureas, j) polyamides, such as e.g. polyamide 6, 6.6, 6.10, 4.6, 4.10, 6.12, 12.12, polyamide 11, polyamide 12 and also (partially) aromatic polyamides, such as e.g. polyphthalamides, e.g. produced from terephthalic acid and/or isophthalic acid and aliphatic diamines or from aliphatic dicarboxylic acids, such as e.g. adipic acid or sebacic acid and aromatic diamines, such as e.g. 1,4- or 1,3-diaminobenzene, k) polyimides, polyamide imides, polyether imides, polyester imides, poly(ether)ketones, polysulphones, polyethersulphones, polyarylsulphones, polyphenylenesulphide, polybenzimidazoles, polyhydantoins, l) polyesters made of aliphatic or aromatic dicarboxylic acids and diols or made of hydroxycarboxylic acids, such as e.g. polyethylene terephthalate (PET), polybutylene terephthalate (PBT), polypropylene terephthalate, polyethylene naphthylate, poly-1,4-dimethylolcyclohexane terephthalate, polyhydroxybenzoate, polyhydroxynaphthalate, polylactic acid, m) polycarbonates, polyester carbonates, and also blends, such as e.g. PC/ABS, PC/PBT, PC/PET/PBT, n) cellulose derivatives, such as e.g. cellulose nitrate, cellulose acetate, cellulose propionate, cellulose butyrate, o) non-thermoplastic or duroplastic plastic materials, p) and also mixtures, combinations or blends made of two or more of the previously mentioned polymers.

Provided that the polymers indicated under a) to o) concern copolymers, these can be present in the form of stochastic ("random"), block- or "tapered" structures.

Provided that the polymers indicated under a) to o) concern stereo-regular polymers, these can be present in the form of isotactic, stereotactic, but also in atactic forms.

Furthermore, the polymers indicated under a) to o) can have both amorphous and (partially) crystalline morphologies.

Possibly, the polyolefins mentioned under a) can also be present in crosslinked form, e.g. crosslinked polyethylene which is then termed X-PE. The polyolefins mentioned under a) can also have any stereo structures, i.e. be present isotactically, syndiotactically or atactically or in stereo block structures.

For very particular preference, the organic oxyimides used according to the invention are used for polyolefins, in particular for the polyolefins mentioned under a).

Furthermore, the present flame retardants can be used in the following duromeric, non-thermoplastic, plastic materials:

q) epoxy resins, consisting of di- or polyfunctional epoxy compounds in combination with e.g, amine-, anhydride- or catalytically-acting hardeners, r) phenol resins, such as e.g. phenol-formaldehyde resins, urea-formaldehyde resins, melamine-formaldehyde resins, s) unsaturated polyester resins, t) silicones, u) polyurethanes as reaction products made of di- or polyfunktional isocyanates and polyols, polyureas, v) alkyde resins, allyl resins.

The flame retardants according to the invention are used for very particular preference in the case of polyolefins, preferably polypropylene and/or polyethylene and the copolymers and blends thereof.

Furthermore, the oxyimide which is used according to the invention can be used in combination with at least one further flame retardant, as a result of which synergistic effects are produced. The at least one further flame retardant is thereby preferably selected from the group consisting of a) inorganic flame retardants, such as e.g. $Al(OH)_3$, $Mg(OH)_2$, $AlO(OH)$, $MgCO_3$, layer silicates, such as e.g. montmorillonite, non- or organically modified, double salts such as e.g. Mg—Al-silicates, POSS-(Polyhedral Oligomeric Silsesquioxane) compounds, huntite, hydromagnesite or halloysite and also $Sb_2O_3$, $Sb_2O_5$, $MoO_3$, zinc stannate, zinc hydroxystannate, b) nitrogen-containing flame retardants, such as e.g. melamine, melem, melam, melon, melamine derivatives, melamine condensation products or melamine salts, benzoguanamine, polyisocyanurates, allantoin, phosphacenes, in particular melamine cyanurate, melamine phosphate, dimelamine phosphate, melamine pyrophosphate, melamine polyphosphate, melamin-metal-phosphates, such as e.g. melamine aluminum phosphate, melamine zinc phosphate, melamine magnesium phosphate, and also the corresponding pyrophosphates and polyphosphates, poly-[2,4-(piperazin-1,4-yl)-6-(morpholin-4-yl)-1,3,5-triazine], ammonium polyphosphate, melamine borate, melamine hydrobromide, c) radical formers, d) phosphorus-containing flame retardants, such as e.g. red phosphorus, phosphates, such as e.g. resorcin diphosphate, bisphenol-A-diphosphate and the oligomers thereof, triphenylphosphate, ethylene diamine diphosphate, phosphinates, such as e.g. salts of hypophosphorous acid and derivatives thereof, such as diethylaluminium phosphinate or aluminium phosphinate, aluminium phosphite, aluminium phosphonate, phosphonate ester, oligomeric and polymeric derivatives of methane phosphonic acid, 9,10-dihydro-9-oxa-10-phosphorylphenanthrene-10-oxide (DOPO) and the substituted compounds thereof, e) halogen-containing flame retardants based on chlorine and bromine, such as e.g polybrominated diphenyloxides, such as e.g. decabromodiphenyl oxide, tris(3-bromo-2,2-bis(bromo-methyl)propyl phosphate, tris (tribromoneopentyl)phosphate, tetrabromophthalic acid, 1,2-bis(tribromophenoxy)ethane, hexabromocyclododecane, brominated diphenylethane, tris-(2,3-dibromopropyl)isocyanurate, ethylene-bis(tetrabromophthalimide), tetrabromobisphenol A, brominated polystyrene, brominated polybutadiene or polystyrene-brominated polybutadiene copolymers, brominated epoxy resin, polypentabromobenzyl acrylate, possibly in combination with $Sb_2O_3$ and/or $Sb_2O_5$, f) borates, such as e.g. zinc borate or calcium borate, g) antidrip agents, such as e.g. polytetrafluorethylene, h) silicon-containing compounds, such as e.g. polyphenylsiloxanes.

The halogen-containing flame retardants mentioned under b) frequently concern commercial products which are commercially available, e.g. from the companies Albemarle, Chemtura/Great Lakes or ICL.

In particular in the case of combinations of the oxyimide used according to the invention with at least one radical former as further flame retardant, synergistic effects result.

Radical formers in the sense of the present invention are compounds which can produce radicals by means of thermal and light-induced cleavage. Suitable radical formers for the applications present here are those which have sufficient thermal stability for the plastic material- or coating-processing processes, i.e. during processing, still form no or only very small quantities of radicals and produce radicals spontaneously only at higher temperatures, as occur only in the case of fire. The respective processing processes and temperatures for coatings and plastic material processing processes are known to the person skilled in the art. Plastic material processing processes and associated temperatures can however also be obtained from the expert literature, such as e.g. H. Domininghaus, P. Elsner, P. Eyerer, T. Hirth, Plastic materials, $8^{th}$ edition, Springer 2012.

The radical former is thereby selected preferably from the group consisting of N-alkoxyamines, —C—C— radical formers, radical formers with azo groups (—N=N—), radical formers with hydrazine groups (—NH—HN—), radical formers with hydrazone groups (>C=N—NH—), radical formers with azine groups (>C=N—N=C<), radical formers with triazene groups (—N=N—N<), radical formers with disulphide- or polysulphide groups (—S—S), radical formers with thiol groups (—S—H), thiuram sulphide, dithiocarbamates, mercaptobenzothiazole and sulphene amides.

The radical former is thereby selected for particular preference from the group consisting of
a) N-alkoxyamines according to the subsequently illustrated structural formula,

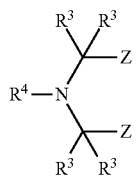

$R^3$ standing for hydrogen or a possibly substituted alkyl, cycloalkyl-, aryl-, heteroaryl- or acyl radical, in particular being a C1 to C4 alkyl radical, $R^4$ standing for an alkoxy-, aryloxy-, cycloalkoxy-, aralkoxy- or acyloxy radical, Z standing for hydrogen or a possibly substituted alkyl, cycloalkyl-, aryl-, heteroaryl- or acyl radical, the two radicals Z also being able to form a closed ring which can be substituted possibly by ester-, ether-, amine-, amide-, carboxy- or urethane groups, b) azo compounds according to the subsequently illustrated structural formulae,

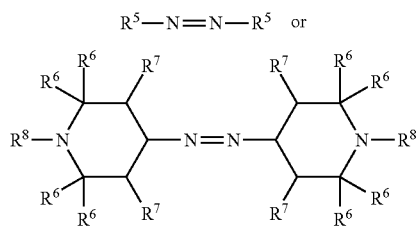

$R^5$ meaning an alkyl-, cycloalkyl- or aryl radical, $R^6$ upon each occurrence, being the same or different and meaning a linear or branched alkyl radical, $R^7$ upon each occurrence, being the same or different and meaning hydrogen or a linear or branched alkyl radical, and $R^8$ upon each occurrence, being the same or different and meaning an alkyl-, alkoxy-, aryloxy-, cycloalkyloxy-, aralkoxy or acyloxy radical, c) dicumyl according to the subsequently illustrated structural formula

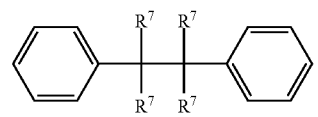

$R^7$ having the previously indicated meaning, preferably being methyl, d) and/or polycumyl according to the subsequently illustrated structural formula

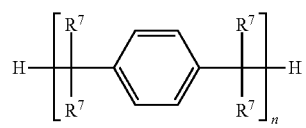

$R^7$ having the previously indicated meaning, preferably being methyl, and $2<n<100$.

Typical examples of the previously mentioned N-alkoxyamines of the indicated structure are thereby:

1-cyclohexyloxy-2,2,6,6-tetramethyl-4-octadecylaminopiperidine; bis(1-octyloxy-2,2,6,6-tetramethylpiperidin-4-yl) sebacate; 2,4-bis[(1-cyclohexyloxy-2,2,6,6-tetramethylpiperidin-4-yl)butylamino]-6-(2-hydroxyethylamino-S-triazine; bis(1-cyclohexyloxy-2,2,6,6-tetramethylpiperidin-4-yl) adipate; 2,4-bis[(1-cyclohexyloxy-2,2,6,6-tetramethylpiperidin-4-yl)butylamino]-6-chloro-S-triazine; 1-(2-hydroxy-2-methylpropoxy)-4-hydroxy-2,2,6,6-tetramethylpiperidine; 1-(2-hydroxy-2-methylpropoxy)-4-oxo-2,2,6,6-tetramethylpiperidine; 1-(2-hydroxy-2-methylpropoxy)-4-octadecanoyloxy-2,2,6,6-tetramethylpiperidine; bis(1-(2-hydroxy-2-methylpropoxy)-2,2,6,6-tetramethylpiperidin-4-yl) sebacate; bis(1-(2-hydroxy-2-methylpropoxy)-2,2,6,6-tetramethylpiperidin-4-yl) adipate; 2,4-bis{N-[1-(2-hydroxy-2-methylpropoxy)-2,2,6,6-tetramethylpiperidin-4-yl]-N-butylamino}-6-(2-hydroxyethylamino)-S-triazine); 4-piperidinol, 2,2,6,6-tetramethyl-1-(undecyloxy)-,4,4'-carbonate; the reaction product of 2,4-bis[(1-cyclohexyloxy-2,2,6,6-tetramethylpiperidin-4-yl)butylamino]-6-chloro-S-triazine with N,N'-bis(3-aminopropylethylenediamine); the oligomer compound, which is the condensation product of 4,4'-hexamethylene-bis(amino-2,2,6,6-tetramethylpiperidine) and 2,4-dichloro-6-[(1-cyclohexyloxy-2,2,6,6-tetramethyl-4-yl)butylamino]-S-triazine, closed at the ends with 2-chloro-4,6-bis(dibutylamino)-S-triazine; aliphatic hydroxylamine, such as e.g. distearyl hydroxylamine; and also compounds of the formula

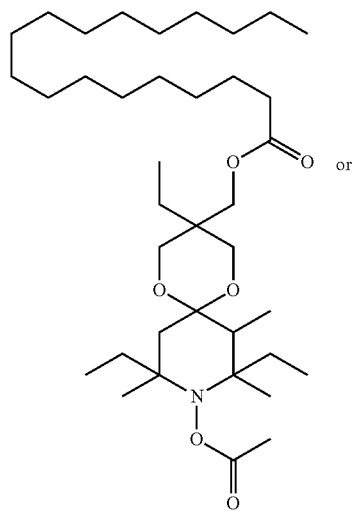

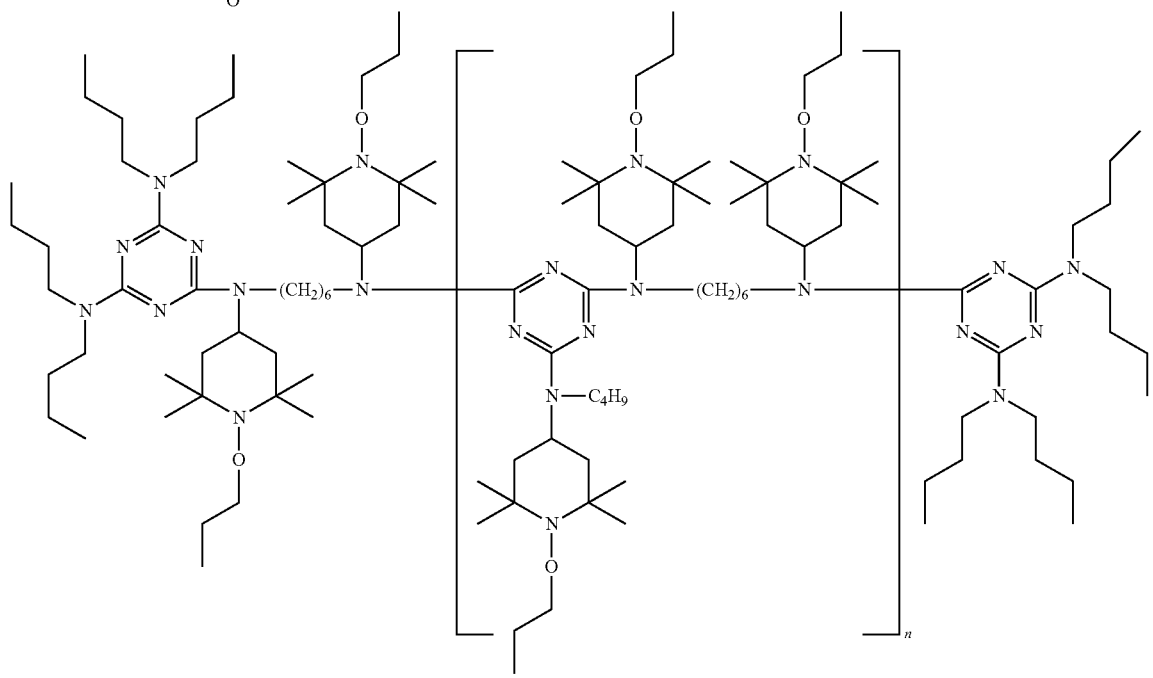

in which n=1-15.

The above-mentioned compounds are partially commercial products and are sold under the following trade names: FLAMESTAB NOR 116®, TINUVIN NOR 371® IRGATEC CR 76® of BASF SE, Hostavin NOW® of Clariant or ADK Stab LA 81® of Adeka. Dicumyl and polycumyl are commercial products which are obtainable for example from United Initiators.

The at least one further flame retardant can be in particular also a phosphorus-containing flame retardant. Preferred phosphorus-containing flame retardants are thereby phosphinates of the following structures:

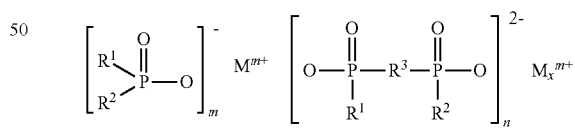

R1 and R2 preferably being identical or different and being selected from linear or branched C1-C6 alkyl and/or aryl; M being selected from the group consisting of Mg, Ca, Al, Sb, Sn, Ge, Ti, Fe, Zr, Ce, Bi, Sr, Mn, Li, Na, K, Zn and/or a protonated nitrogen base, preferably calcium ions, magnesium ions, aluminium ions and/or zinc ions; and m=1-4, preferably 2 or 3; n=1-4, preferably 1 or 3; x=1-4, preferably 1 or 2. In a particularly preferred embodiment, $R_1$=alkyl, $R_2$=alkyl and M=Al or Zn.

A particularly preferred example of a phosphinate according to the invention is the commercially available products Exolit OP® of Clariant SE.

Further preferred phosphorus-containing flame retardants are metal salts of hypophosphorous acid with a structure according to the formula

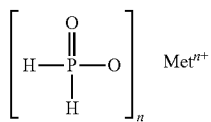

Met being a metal, selected from groups I, II, III and IV of the periodic table of elements, and n being a number from 1 to 4 which corresponds to the charge of the corresponding metal ion Met. Met is for example $Na^+$, $Ca^{2+}$, $Mg^{2+}$, $Zn^{2+}$, $Ti^{4+}$ or $Al^{3+}$, wherein $Ca^{2+}$, $Zn^{2+}$ and $Al^{3+}$ are particularly preferred.

The above-mentioned salts of hypophosphorous acid are partially commercially available, e.g. with the title Phoslite® of Italmatch Chemicals.

A further preferred group of phosphorus-containing flame retardants are phosphonates or phosphonic acid diaryl esters of a structure according to the following formula:

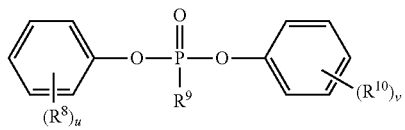

$R_8$ and $R_{10}$=H, alkyl, preferably C1-C4 alkyl, $R_9$=C1-C4 alkyl, u=1-5 and v=1-5.

Corresponding structures can also be present in the form of phosphonate oligomers, polymers and co-polymers. Linear or branched phosphonate oligomers and polymers are known from the state of the art. For branched phosphonate oligomers and polymers, reference is made to the US patents U.S. Pat. No. 2,716,101, U.S. Pat. No. 3,326,852, U.S. Pat. No. 4,328,174, U.S. Pat. No. 4,331,614, U.S. Pat. No. 4,374,971, U.S. Pat. No. 4,415,719, U.S. Pat. No. 5,216,113, U.S. Pat. No. 5,334,692, U.S. Pat. No. 3,442,854, U.S. Pat. No. 6,291,630 B1, U.S. Pat. No. 6,861,499 B2 and U.S. Pat. No. 7,816,486 B2. For phosphonate oligomers, reference is made to the US patent applications US 2005/0020800 A1, US 2007/0219295 A1 and US 2008/0045673 A1. With respect to linear phosphonate oligomers and polymers, reference is made to the US patent documents U.S. Pat. No. 3,946,093, U.S. Pat. No. 3,919,363, U.S. Pat. No. 6,288,210 B1, U.S. Pat. No. 2,682,522 and U.S. Pat. No. 2,891,915.

Phosphonates are available for example under the trade name Nofia® of FRX Polymers.

A further preferred group of phosphorus-containing flame retardants are compounds based on oxaphosphorine oxide and derivatives thereof with for example the following structures:

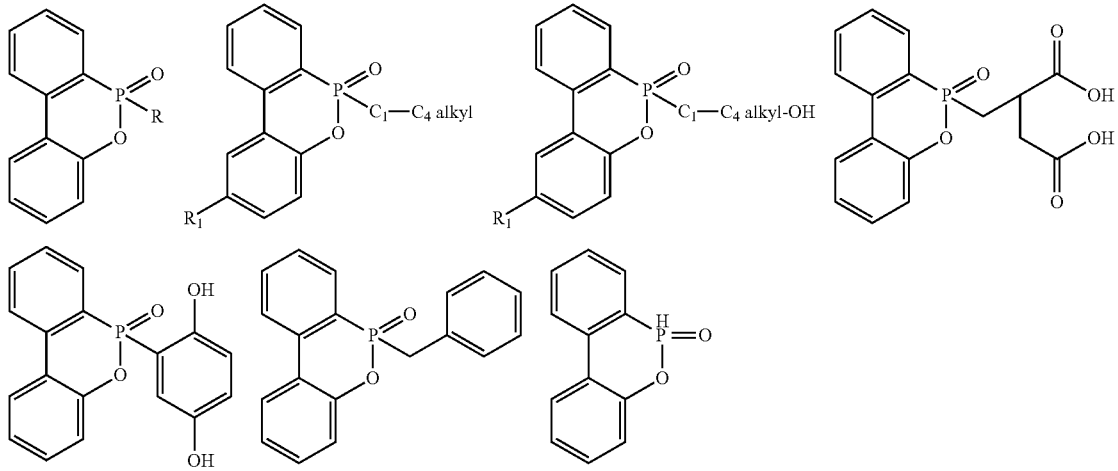

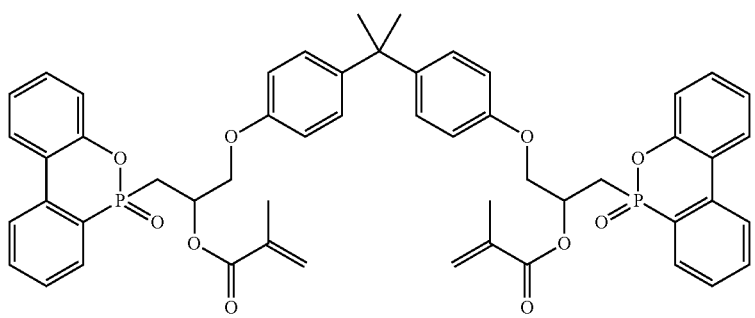

-continued
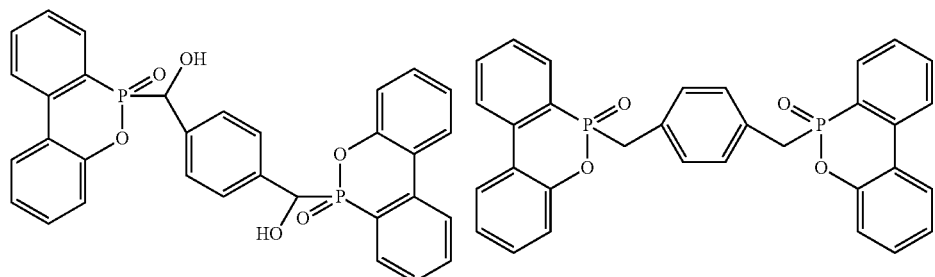
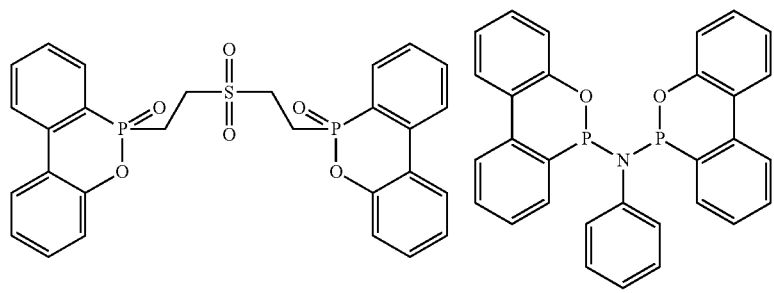
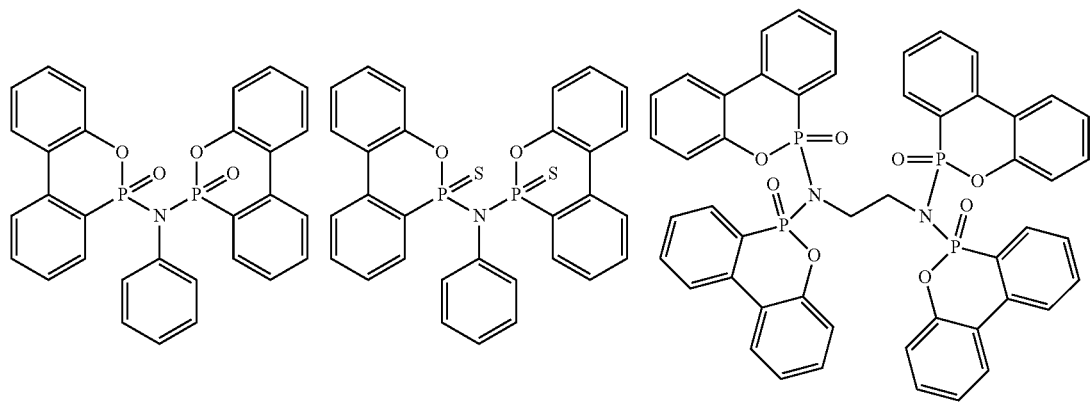
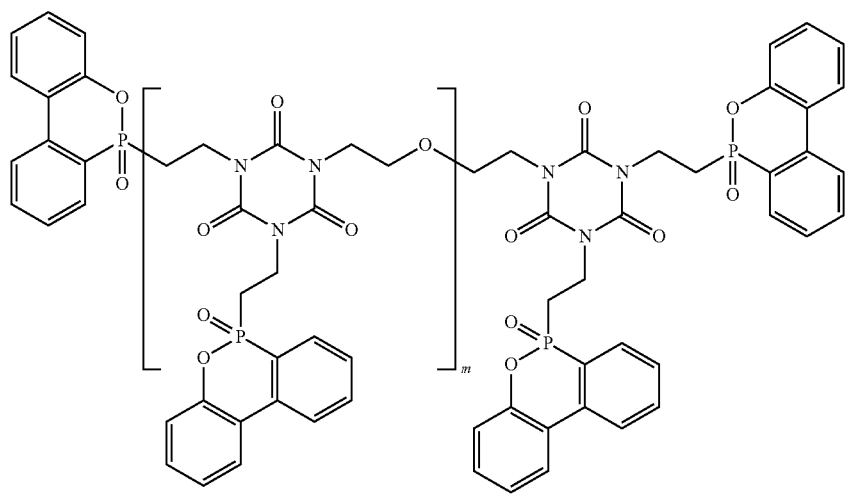

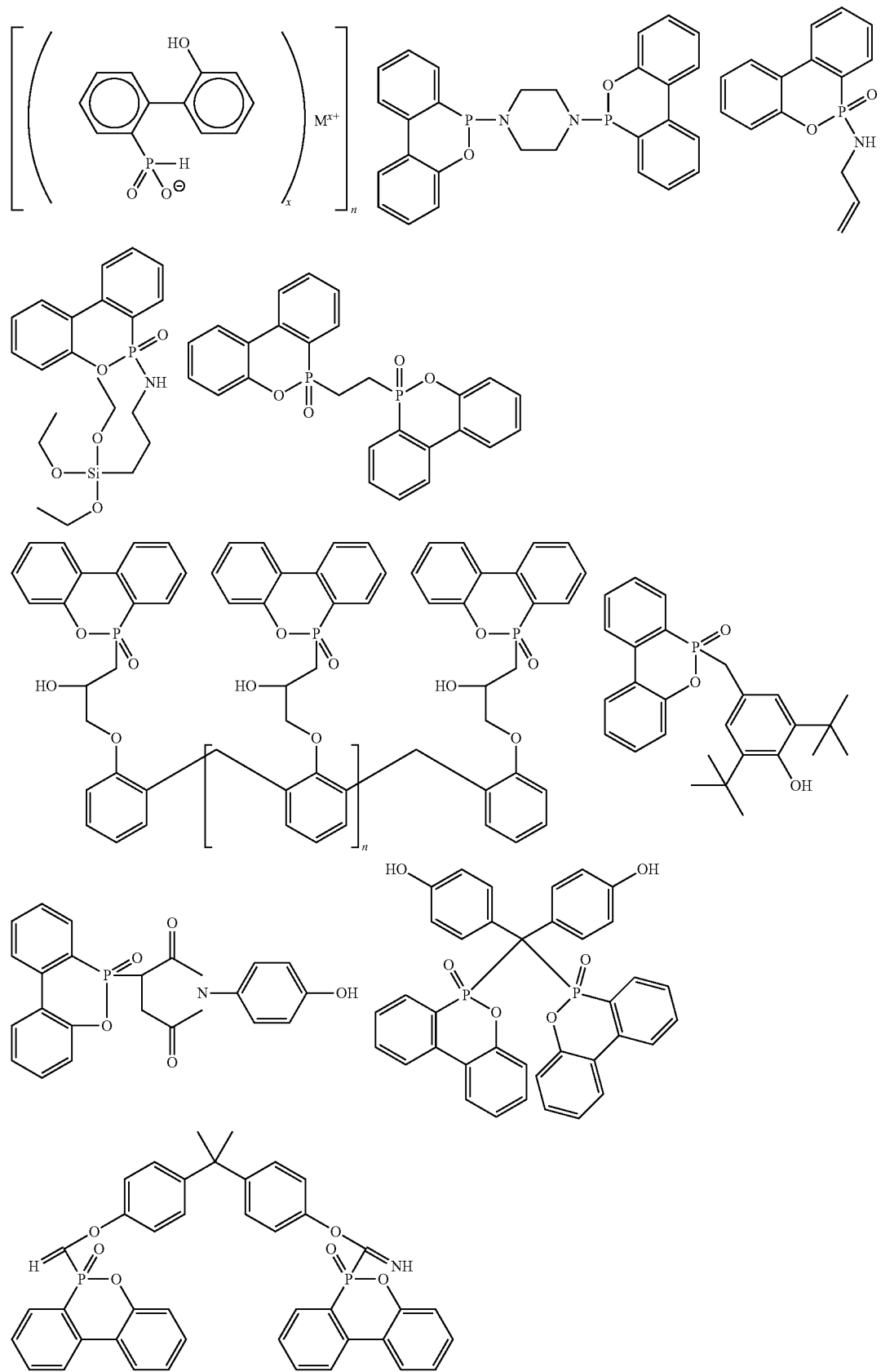

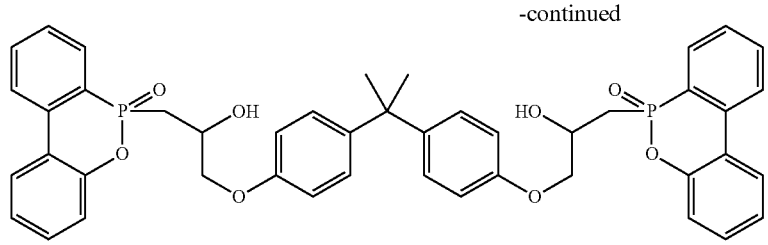

M being a metal, selected from the second, third, twelfth or thirteenth group of the periodic table of the elements, x=2 or 3, n≥10, m=0-25, R=H, halogen or an aliphatic or aromatic radical with 1-32 C atoms and $R_1$=H, C1-C6 alkyl.

Products based on oxaphosphorine oxide are marketed for example under the trade name Ukanol® of Schill and Seilacher GmbH. Further compounds can be produced for example according to the patent specifications WO 2013020696, WO 2010135398, WO 03070736, WO 2006084488, WO 2006084489, WO 2011000019, WO 2013068437, WO 2013072295.

Further synergistic phosphorus-containing flame retardants are cyclic phosphonates of a structure according to one of the following formulae:

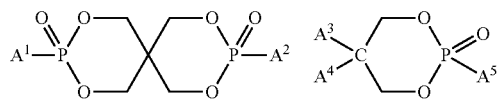

$A^1$ and $A^2$, independently of each other, representing a substituted or unsubstituted, straight-chain or branched alkyl group with 1 to 4 carbon atoms, substituted or unsubstituted benzyl, substituted or unsubstituted phenyl, substituted or unsubstituted naphthyl, and $A^3$ and $A^4$, independently of each other, being methyl or ethyl and $A^5$ being a straight-chain or branched alkyl group with 1 to 4 carbon atoms or a phenyl- or benzyl group which can have respectively up to 3 methyl groups.

Cyclic phosphonates are marketed for example by the company Thor GmbH under the trade name Aflammit® or can be produced according to EP 2450401.

The at least one further flame retardant can be in particular also a nitrogen-containing flame retardant. Preferred nitrogen-containing flame retardants are melamine polyphosphate, melamine cyanurate, melamine-metal phosphates, poly-[2,4-(piperazin-1,4-yl)-6-(morpholin-4-yl)-1,3,5-triazine] and ammonium polyphosphate. These compounds are commercial products and obtainable under the trade names Melapur® of BASF SE, Budit® of Budenheim Chemische Fabrik, Exolit® of Clariant, Safire® of Floridienne or MCA PPM triazine of MCA Technologies GmbH.

In the case of a combined use of the oxyimide used according to the invention with at least one further flame retardant, it is preferred if the previously mentioned compounds are used in a weight ratio (oxyimide:flame retardant) of 99:1 to 1:99, preferably of 5:95 to 50:50, particularly preferred of 10:90 to 30:70.

Furthermore, it is advantageous if the organic oxyimides, relative to the plastic materials, are used at 0.01 to 30% by weight, preferably at 0.1 to 20% by weight, particularly preferred at 1 to 10% by weight.

In addition, the present invention relates to a flame-retardant plastic material composition, comprising or consisting of
a) 50 to 98 parts by weight, preferably 70 to 95 parts by weight, of at least one plastic material, in particular of at least one thermoplastic polymer,
b) 1 to 25 parts by weight, preferably 2.5 to 15 parts by weight, of at least one organic oxyimide, comprising at least one structural element of the subsequently illustrated formula I,

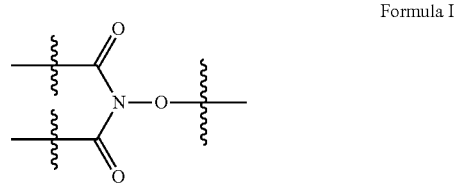 [SMILES: *ON(C(*)=O)C(*)=O]

Formula I the organic oxyimide being halogen-free,
c) 1 to 25 parts by weight, preferably 2.5 to 15 parts by weight, of at least one further flame retardant.

According to a preferred embodiment, the flame-retardant plastic material composition can comprise in addition
a) up to 40 parts by weight of at least one reinforcing- or filling material and/or
b) up to 5 parts by weight of at least one additive from the class of phenolic antioxidants, phosphites, acid collectors, hindered amines, dispersants and also combinations hereof.

In addition, additives can be used, selected from the group consisting of UV absorbers, light stabilisers, stabilisers, hydroxylamines, benzofuranones, metal deactivators, filler deactivators, nucleation agents, impact strength enhancers, plasticisers, lubricants, rheology modifiers, processing aids, pigments, colourants, optical brighteners, antimicrobial active substances, antistatic agents, slip agents, antiblocking agents, coupling means, dispersants, compatibilisers, oxygen collectors, acid collectors, marking means or antifogging means. In a preferred embodiment, the compositions comprise in particular acid collectors, e.g. based on salts of long-chain acids, such as e.g. calcium stearate, magnesium stearate, zinc stearate, calcium lactate or hydrotalcites and/or stabilisers from the group of phenolic antioxidants and phosphites/phosphonites and/or light stabilisers from the group of hindered amines (HALS) and/or dispersants.

Suitable light stabilisers are for example compounds based on 2-(2'-hydroxyphenyl)benzotriazoles, 2-hydroxybenzophenones, esters of benzoic acids, acrylates, oxamides and 2-(2-hydroxyphenyl)-1,3,5-triazines.

Suitable 2-(2"-hydroxyphenyl)benzotriazoles are for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxy-phenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'12-methoxycarbonylethyl)phenyl)benzotriazole, 2-(3'-tert-butyl-2'-hydroxy-5'12-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazol-2-ylphenol]; the product of reesterification of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$, with R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)phenyl]benzotriazole, 2-[2'-hydroxy-3'-(1,1,3,3-tetramethylbutyl)-5'-(α,α-dimethylbenzyl)phenyl]benzotriazole.

Suitable 2-hydroxybenzophenones are for example 4-hydroxy-, 4-methoxy-, 4-octyloxy-, 4-decyloxy-4-dodecyloxy, 4-benzyloxy, 4,2',4'-trihydroxy- and 2'-hydroxy-4,4'-dimethoxy derivatives of 2-hydroxybenzophenones.

Suitable acrylates are for example ethyl-α-cyano-β,β-diphenylacrylate, isooctyl-α-cyano-β,β-diphenylacrylate, methyl-α-carbomethoxycinnamate, methyl-α-cyano-β-methyl-β-methoxycinnamate, butyl-α-cyano-β-methyl-p-methoxycinnamate, methyl-α-carbomethoxy-p-methoxycinnamate and N-(β-carbomethoxy-β-cyanoyinyl)-2-methylindoline.

Suitable esters of benzoic acids are for example 4-tert-butylphenylsalicylate, phenylsalicylate, octylphenylsalicylate, dibenzoylresorcinol, bis(4-tert-butylbenzoyl)resorcinol, benzoylresorcinol, 2,4-di-tert-butylphenyl-3, 5-di-tert-butyl-4-hydroxybenzoate, hexadecyl-3, 5-di-tert-butyl-4-hydroxybenzoate, octadecyl-3, 5-di-tert-butyl-4-hydroxybenzoate, 2-methyl-4,6-di-tert-butylphenyl-3, 5-di-tert-butyl-4-hydroxybenzoate.

Suitable oxamides are for example 4,4'-dioctyloxyoxanilide, 2,2'-diethoxyoxanilide, 2,2'-dioctyloxy-5, 5'-di-tert-butoxanilide, 2,2'-didodecyloxy-5, 5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and the mixtures thereof with 2-ethoxy-2'-ethyl-5,4'-di-tert-butoxanilide, mixtures of o- and p-methoxy-disubstituted oxanilides and mixtures of o- and p-ethoxy-disubstituted oxanilides.

Suitable 2-(2-hydroxyphenyl)-1,3,5-triazines are for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)-phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl-1,3,5-triazine.

Suitable metal deactivators are for example N,N'-diphenyloxamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyldihydrazide, oxanilide, isophthaloyldihydrazide, sebacoylbisphenylhydrazide, N,N'-diacetyladipoyldihydrazide, N,N'-bis(salicyloyl)oxylyldihydrazide, N,N'-bis(salicyloyl)thiopropionyldihydrazide.

In particular, the following structures are suitable as metal deactivators:

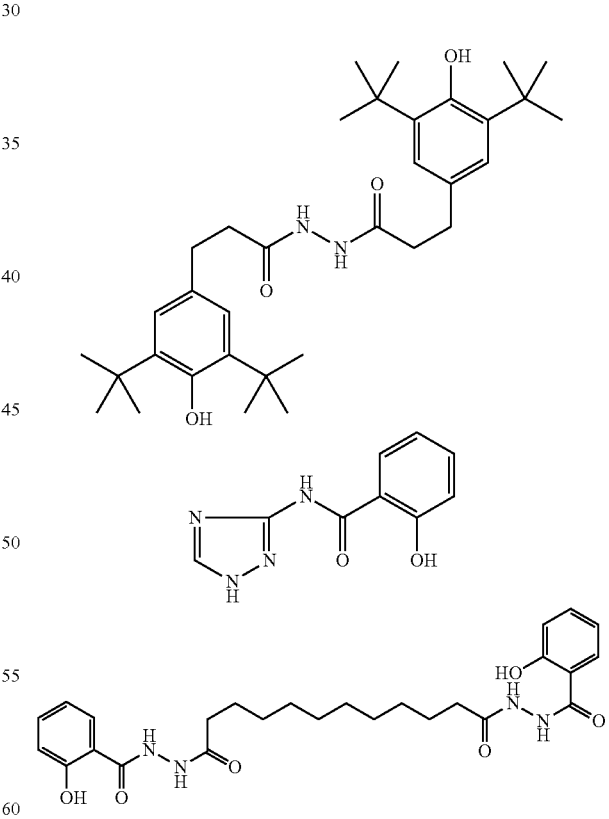

Suitable phenolic antioxidants are for example:
alkylated monophenols, such as e.g. 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6- dimethylphenol, 2,6-dioctadecyl-4-methylphenol, 2,4,6-tricyclohexylphenol, 2,6-di-tert-butyl-4-methoxymethylphenol, linear or branched nonylphenols, such as e.g. 2,6-dinonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures hereof;

alkylthiomethylphenols, such as e.g. 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol;

hydroquinones and alkylated hydroquinones, such as e.g. 2,6-di-tert-butyl-4-methyoxyphenol, 2, 5-di-tert-butylhydroquinone, 2, 5-di-tert-amylhydroquinone, 2,6-diphenyl-4-octadecyloxyphenol, 2,6-di-tert-butylhydroquinone, 2, 5-di-tert-butyl-4-hydroxyanisole, 3, 5-di-tert-butyl-4-hydroxyanisole, 3, 5-di-tert-butyl-4-hydroxyphenylstearate, bis(3, 5-di-tert-butyl-4-hydroxylphenyl)adipate;

tocopherols, such as e.g. α-, β-, γ-, δ-tocopherol and mixtures of these (vitamin E);

hydroxylated thiodiphenylethers, such as e.g. 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulphide;

alkylidenebisphenols, such as e.g. 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclhexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethyleneglycol-bis[3,3-bis(3'-tert-butyl-4'-hydroxyphenyl) butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis-(3, 5-dimethyl-2-hydroxyphenyl)butane, 2,2-bis(3, 5-di-tert-butyl-4-hydroxyphenyl)propane, 2,2-bis-(5-tert-butyl-4-hydroxy-2-methylphenyl)-4-n-dodecylmercaptobutane, 1,1, 5, 5-tetra(5-tert-butyl-4-hydroxy-2-methylphenyl)pentane;

O-, N- and S-benzyl compounds, such as e.g. 3,5,3',5'-tetra-tert-butyl-4,4'-dihydroxydibenzylether, octadecyl-4-hydroxy-3,5-dimethylbenzylmercaptoacetate, tridecyl-4-hydroxy-3, 5-di-tert-butylbenzylmercaptoacetate, tris(3, 5-di-tert-butyl-4-hydroxybenzyl)amine, bis(4-tert-butyl-3-hydroxy-2, 6-dimethylbenzyl)dithioterephthalate, bis(3,5-di-tert-butyl-4-hydroxybenzyl) sulphide, isooctyl-3,5-di-tert-butyl-4-hydroxybenzylmercaptoacetate;

hydroxybenzylated malonates, such as e.g. dioctadecyl-2,2-bis(3,5-di-tert-butyl-2-hydroxybenzyl)malonate, dioctadecyl-2-(3-tert-butyl-4-hydroxy-5-methylbenzyl)malonate, didodecylmercaptoethyl-2,2-bis(3, 5-di-tert-butyl-4-hydroxybenzyl)malonate, bis[4-(1,1,3,3-tetramethylbutyl)phenyl]-2,2-bis(3, 5-di-tert-butyl-4-hydroxybenzyl)malonate;

aromatic hydroxybenzyl compounds, such as e.g. 1,3,5-tris(3, 5-di-tert-butyl-4-hydroxybenzyl)-2,4,6-trimethylbenzene, 1,4-bis(3, 5-di-tert-butyl-4-hydroxybenzyl)-2,3,5,6-tetramethylbenzene, 2,4,6-tris(3, 5-di-tert-butyl-4-hydroxybenzyl)phenol;

triazine compounds, such as e.g. 2,4-bis(octylmercapto)-6-(3, 5-di-tert-butyl-4-hydroxyanilino)-1,3,5-triazine, 2-octylmercapto-4,6-bis(3, 5-di-tert-butyl-4-hydroxyanilino)-1, 3,5-triazine, 2-octylmercapto-4,6-bis(3, 5-di-tert-butyl-4-hydroxyphenoxy)-1,3,5-triazine, 2,4,6-tris(3, 5-di-tert-butyl-4-hydroxyphenoxy)-1,2,3-triazine, 1,3,5-tris(3, 5-di-tert-butyl-4-hydroxybenzyl)isocyanurate, 1,3,5-tris(4-tert-butyl-3-hydroxy-2, 6-dimethylbenzyl)isocyanurate, 2,4,6-tris(3, 5-di-tert-butyl-4-hydroxphenylethyl)-1,3,5-triazine, 1,3,5-tris(3, 5-di-tert-butyl-4-hydroyphenylpropionyl)hexahydro-1,3,5-triazine, 1,3,5-tris(3,5-dicyclohexyl-4-hydroxybenzyl)isocyanurate;

benzylphosphonates, such as e.g. dimethyl-2, 5-di-tert-butyl-4-hydroxybenzylphosphonate, diethyl-3, 5-di-tert-butyl-4-hydroxybenzylphosphonate, dioctadecyl-3, 5-di-tert-butyl-4-hydroxybenzylphosphonate, dioctadecyl-5-tert-butyl-4-hydroxy-3-methylbenzylphosphonate, the calcium salt of the monoethylester of 3,5-di-tert-butyl-4-hydroxybenzylphosphonic acid;

acylaminophenols, such as e.g. 4-hydroxylauranilide, 4-hydroxystearanilide, octyl-N-(3, 5-di-tert-butyl-4-hydroxyphenyl)carbamate;

esters of β-(3,5-di-tert-butyl-4-hydroxyphenyl)propionic acid with mono- or multivalent alcohols, e.g. methanol, ethanol, n-octanol, i-octanol, octadecanol, 1,6-hexanediol, 1,9-nonanediol, ethyleneglycol, 1,2-propanediol, neopentylglycol, thiodiethyleneglycol, diethyleneglycol, triethyleneglycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane, esters of β-(5-tert-butyl-4-hydroxy-3-methylphenyl)propionic acid with mono- or multivalent alcohols, e.g. methanol, ethanol, n-octanol, i-octanol, octadecanol, 1,6-hexanediol, 1,9-nonanediol, ethyleneglycol, 1,2-propanediol, neopentylglycol, thiodiethyleneglycol, diethyleneglycol, triethylenerglycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6, 7-trioxabicyclo[2.2.2]octane, 3,9-bis[2-{3-(3-tert-butyl-4-hydroxy-5-methylphenyl)propionyloxy}-1,1-dimethylethyl]-2,4,8,10-tetraoxaspiro[5.5]undecane;

esters of β-(3,5-dicyclohexyl-4-hydroxyphenyl)propionic acid with mono- or multivalent alcohols, e.g. methanol, ethanol, octanol, octadecaneol, 1,6-hexanediol, 1,9-nonanediol, ethyleneglycol, 1,2-propanediol, neopentylglycol, thiodiethyleneglycol, diethyleneglycol, triethyleneglycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane;

esters of 3,5-di-tert-butyl-4-hydroxyphenyl)acetic acid with mono- or multivalent alcohols, e.g. methanol, ethanol, octanol, octadecanol, 1,6-hexanediol, 1,9-nonanediol, ethyleneglycol, 1,2-propanediol, neopentylglycol, thiodiethyleneglycol, diethyleneglycol, triethyleneglycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane;

amides of β-(3,5-di-tert-butyl-4-hydroxyphenyl)propionic acid, such as e.g. N,N'-bis(3, 5-di-tert-butyl-4-hydroxyphenylpropionyl)hexamethylenediamide, N,N'-bis(3,5-di-tert-butyl-4-hydroxyphenylpropionyl)hexamethylenediamide, N,N'-bis(3,5-di-tert-butyl-4-hydroxyphenylpropionyl)hexamethylenediamide, N,N'-bis(3, 5-di-tert-butyl-4-hydroxyphenylpropionyl)hydrazide, N,N'-bis[2-(3-[3, 5-di-tert-butyl-4-hydroxyphenyl]propionyloxy) ethyl]oxamide (Naugard®XL-1, marketed by Uniroyal);

ascorbic acid (vitamin C).

Particularly preferred phenolic antioxidants are:

octadecyl-3-(3, 5-di-tert-butyl-4-hydroxyphenyl)propionate, pentaerythritol-tetrakis[3-(3, 5-di-tert-butyl-4-hydroxyphenyl)propionate, tris(3, 5-di-tert-butyl-4-hydroxyphenyl)isocyanurate, 1,3,5-trimethyl-2,4,6-tris(3, 5-di-tert-butyl-4-hydroxyphenyl)isocyanurate, 1,3,5-trimethyl-2,4,6-tris(3, 5-di-tert-butyl-4-hydroxybenzyl)benzene, triethyleneglycol-bis[3-(3-tert-butyl-4-hydroxy-5-methylphenyl)propionate, N,N'-hexan-1, 6-diyl-bis[3-(3, 5-di-tert-butyl-4-hydroxyphenyl)propionic acid amide.

Suitable phosphites/phosphonites are for example:

triphenylphosphite, diphenylalkylphosphites, phenyldialkylphosphites, tri(nonylphenyl)phosphite, trilaurylphosphites, trioctadecylphosphite, distearylpentaerythritoldiphosphite, tris-(2,4-di-tert-butylphenyl)phosphite, diisodecylpentaerythritoldiphosphite, bis(2,4-di-tert-butylphenyl)pentaerythritoldiphosphite, bis(2,4-di-cumylphenyl)pentaerythritoldiphosphite, bis(2,6-di-tert-butyl-4-methylphenyl)pentaerythritoldiphosphite, diisodecyloxypentaerythritoldiphosphite, bis(2,4-di-tert-butyl-6-methylphenyl)pentaerythritoldiphosphite, bis(2,4,6-tris(tert-butylphenyl)pentaerythritoldiphosphite, tristearylsorbitoltriphosphite, tetrakis(2,4-di-tert-butylphenyl)-4,4-biphenylenediphosphonite, 6-isooctyloxy-2,4,8,10-tetra-tert-butyl-12H-dibenzo[d,g]-1, 3,2-dioxaphosphocine, bis (2,4-di-tert-butyl-6-methylphenyl)methylphosphite, bis(2,4-di-tert-butyl-6-methylphenyl)ethylphosphite, 6-fluoro-2,4, 8,10-tetra-tert-butyl-12-methyl-dibenzo[d, g]-1,3,2-dioxaphosphocine, 2,2'2"-nitrilo[triethyltris(3,3",5,5'-tetra-tert-butyl-1,1'-biphenyl-2,2'-diyl)phosphite], 2-ethylhexyl (3,3',5,5'-tetra-tert-butyl-1,1'-biphenyl-2,2'-diyl))phosphite, 5-butyl-5-ethyl-2-(2,4,6-tri-tert-butylphenoxy)-1,3,2-dioxaphosphirane.

Particularly preferred phosphites/phosphonites are:

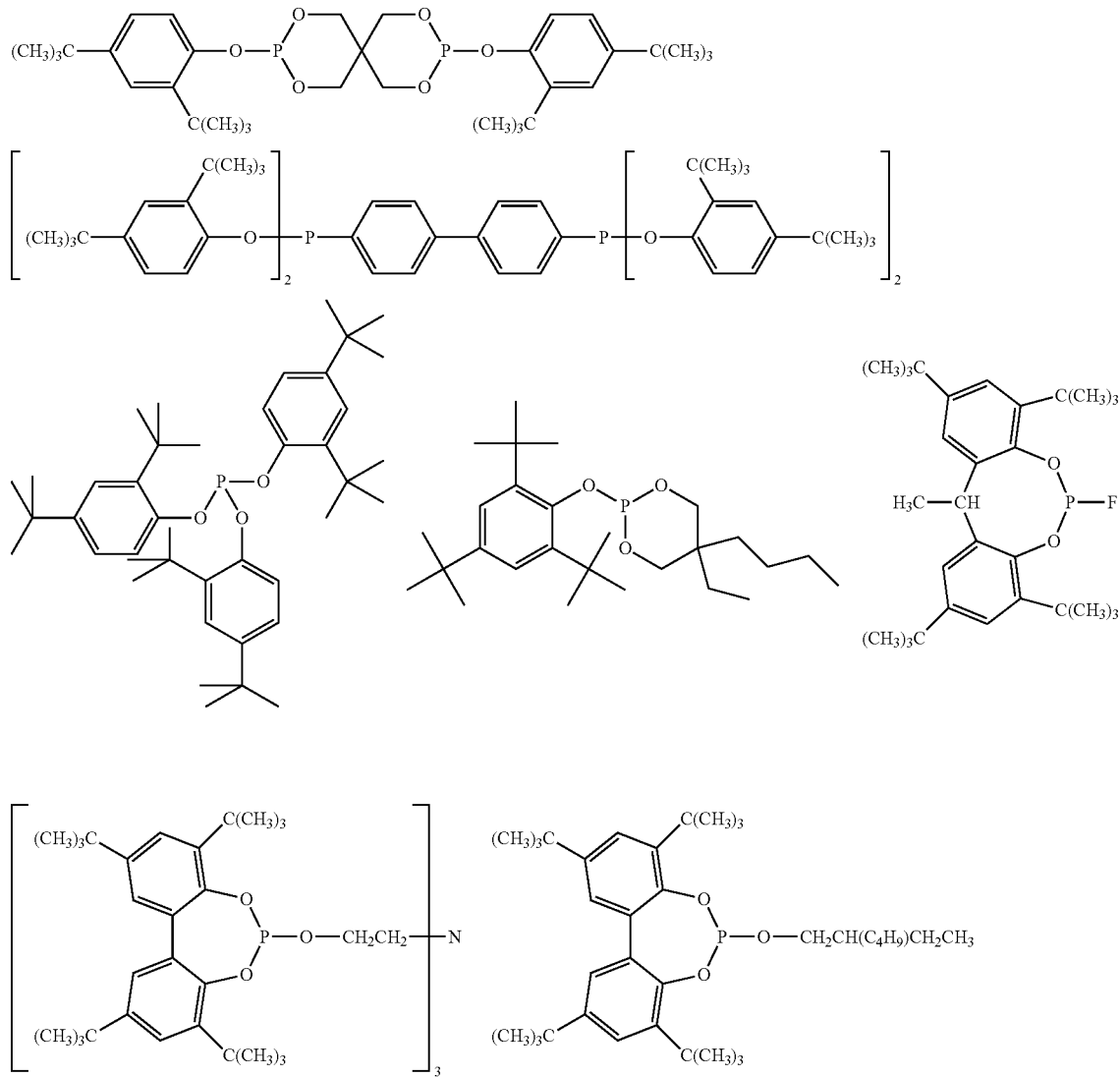

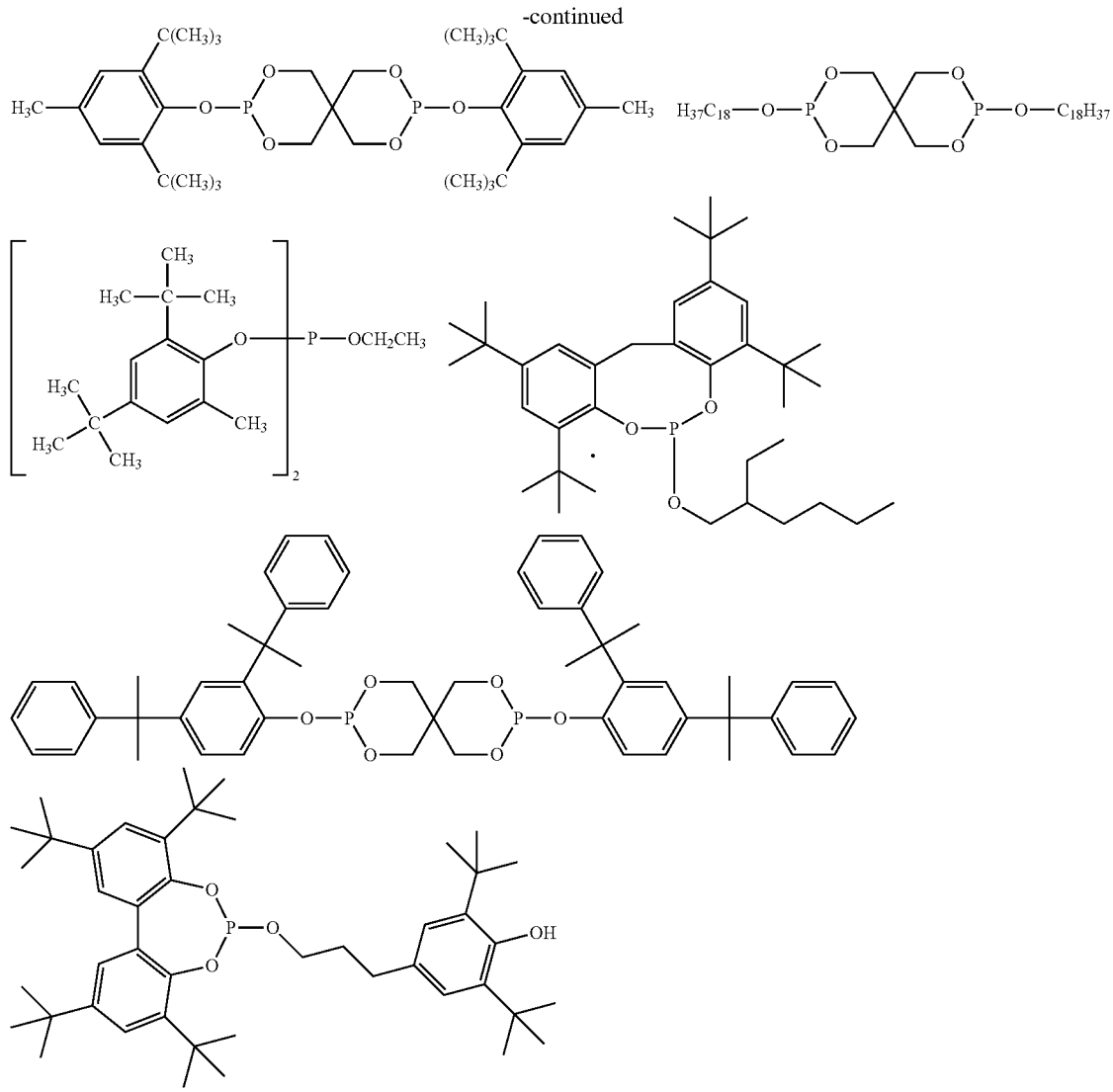

Further suitable stabilisators are amine antioxidants. Suitable amine antioxidants are for example:

N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N,N'-phenyl-p-phenylenediamine, N-(1-methylheptyl)-N,N'-phenyl-p-phenylenediamine, N-cyclohexyl-N'-phenyl-p-phenylenediamine, 4-(p-toluenesulfamoyl)diphenylamine, N,N '-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, e.g. p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene and also mixtures or combinations hereof.

Further suitable amine antioxidants are hydroxylamines, or N-oxides (nitrons), such as e.g. N,N-dialkylhydroxylamines, N,N-dibenzylhydroxylamine, N,N-dilaurylhydroxylamine, N,N-distearylhydroxylamine, N-benzyl-α-phenylnitron, N-octadecyl-α-hexadecylnitron, and also Genox EP (Chemtura) according to the formula:

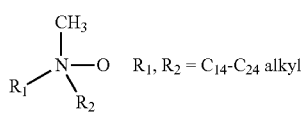

Further suitable stabilisers are thiosynergists. Suitable thiosynergists are for example, distearylthiodipropionate, dilauryldipropionate or the compound according to the following formula:

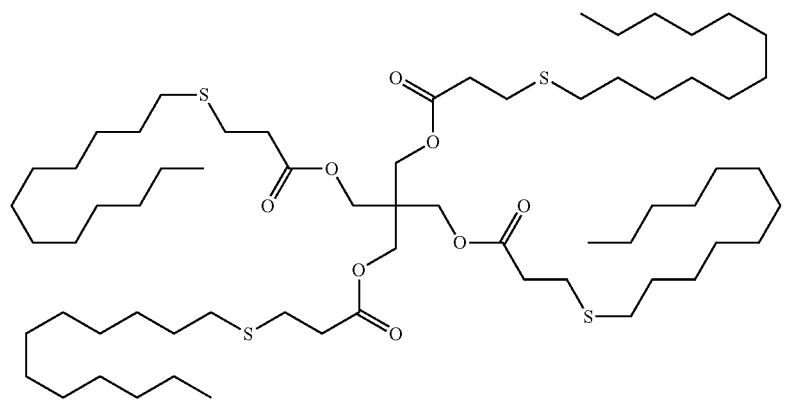 [SMILES: CCCCCCCCCCCCSCCC(=O)OCC(COC(=O)CCSCCCCCCCCCCCC)(COC(=O)CCSCCCCCCCCCCCC)COC(=O)CCSCCCCCCCCCCCC]

Further suitable stabilisers, in particular for polyamides, are copper salts, such as e.g. copper(I)iodide, copper(I) bromide or copper complexes, such as e.g. triphenylphosphine-copper(I) complexes.

Suitable hindered amines are for example 1,1-bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl)-n-butyl-3,5-di-tert-butyl-4-hydroxybenzylmalonate, the condensation product of 1-(2-hydroxyethyl)-2,2,6,6-tetramethyl-4-hydroxypiperidine und succinic acid, linear or cyclic condensation products of N,N'-bis(2,2,6,6-tetramethyl-4-piperidyl)hexamethylenediamine and 4-tert-octylamino-2,6-di-chloro-1,3,5-triazine, tris(2,2,6,6-tetramethyl-4-piperidyl)nitrilotriacetate, tetrakis (2,2,6,6-tetramethyl-4-piperidyl)-1,2,3,4-butanetetracarboxylate, 1,1'-(1,2-ethandiyl)-bis(3,3,5,5-tetramethylpiperazinone), 4-benzoyl-2,2,6,6-tetramethylpiperidine, 4-stearyloxy-2,2,6,6-tetramethylpiperidine, linear or cyclic condensation products of N,N'-bis(2,2,6,6-tetramethyl-4-piperidyl)hexamethylenediamine and 4-morpholino-2,6-dichloro-1,3,5-triazine, the reaction product of 7,7,9,9-tetramethyl-2-cycloundecyl-1-oxa-3,8-diaza-4-oxospiro-[4,5] decane und epichlorhydrin.

Suitable dispersants are for example:
polyacrylates, e.g. copolyers with long-chain side groups, polyacrylate block copolymers, alkylamides: e.g. N,N'-1,2-ethandiylbisoctadecaneamide sorbitan ester, e.g. monostearyl sorbitan ester, titanates und zirconates, reactive copolymers with functional groups, e.g. polypropylene-co-acrylic acid, polypropylene-co-maleic anhydride, polyethylene-co-glycidylmethacrylate, polystyrene-alt-maleic anhydride-polysiloxanes: e.g. dimethylsilanediol-ethylene oxide copolymer, polyphenylsiloxane copolymer, amphiphilic copolymers: e.g. polyethylene-block-polyethylenoxide, dendrimers, e.g. hydroxyl group-containing dendrimers.

Suitable nucleation agents are for example talc, alkali or alkaline earth salts of mono- and polyfunctional carboxylic acids, such as e.g. benzoic acid, succinic acid, adipic acid, e.g. sodium benzoate, zinc glycerolate, aluminium hydroxybis(4-tert-butyl)benzoate, benzylidenesorbitols, such as e.g. 1,3:2,4-bis(benzylidene)sorbitol or 1,3:2,4-bis(4-methylbenzylidene)sorbitol, 2,2''-methylene-bis-(4,6-di-tert-butylphenyl)phosphate, and also trisamides, such as e.g according to the following structures

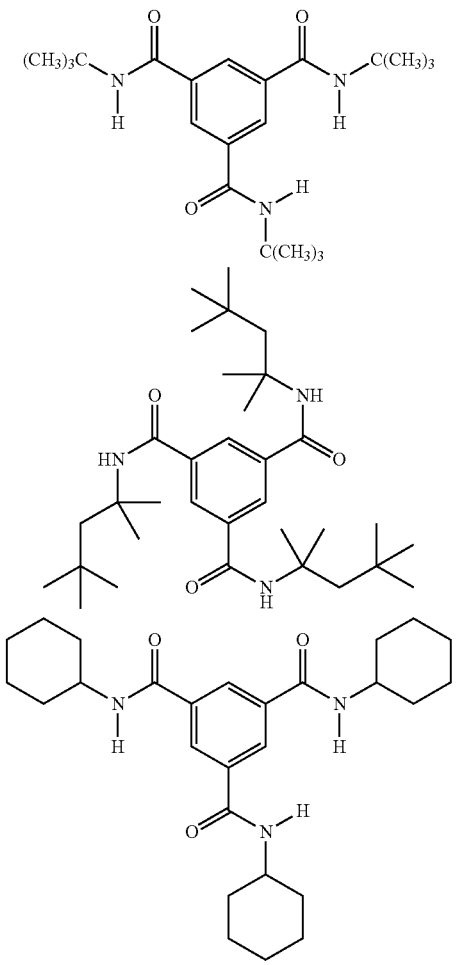

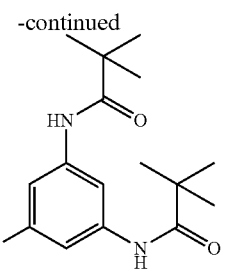

Suitable fillers and reinforcing materials are for example synthetic or natural materials, such as e.g. calcium carbonate, silicates, glass fibres, glass balls (solid or hollow), talc, mica, kaolin, barium sulphate, metal oxides and metal hydroxides, carbon black, graphite, carbon nanotubes, graphene, sawdust or fibres from natural products, such as e.g. cellulose, or synthetic fibres. Further suitable fillers are hydrotalcites or zeolites or layer silicates, such as e.g. montmorrillonite, bentonite, beidelite, mica, hectorite, saponite, vermiculite, ledikit, magadite, illite, kaolinite, wollastonite, attapulgite.

Suitable pigments can be of an inorganic or organic nature. Suitable inorganic pigments are for example titanium dioxide, zinc oxide, zinc sulphide, iron oxide, ultramarine, carbon black. Suitable organic pigments are for example anthraquinones, anthanthrones, benzimidazolones, quinacridones, diketopyrrolopyrroles, dioxazines, indanthrones, isoindolinones, azo compounds, perylenes, phthalocyanines or pyranthrones. Further suitable pigments are effect pigments on a metal base or pearlescent pigments on a metal oxide base.

Optical brighteners are for example bisbenzoxazoles, phenylcumarines or bis(styryl)biphenyls and in particular optical brighteners of the formulae:

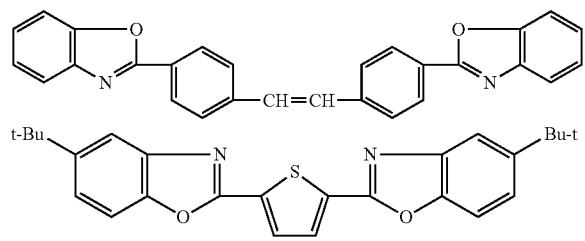

Suitable filler deactivators are for example epoxides, such as e.g. bisphenol-A-diglycidyl ethers, polysiloxanes, polyacrylates, in particular block copolymers such as polymethacrylic acid-polyalkylene oxide.

Suitable antistatic agents are for example ethoxylated alkylamines, fatty acid esters, alkyl sulphonates and polymers such as e.g. polyether amides.

Furthermore, the present invention relates to a moulding compound, a moulded part, a paint or a coating producible from a previously described flame-retardant plastic material composition, in particular in the form of injection moulded parts, foils or films, coatings or paints, foams, fibres, cables and pipes, profiles, strips, membranes, such as e.g. geomembranes, adhesives, which are produced by extrusion, injection moulding, blow-moulding, calendering, pressing processes, spinning processes or brushing and coating processes, e.g. for the electrical and electronic industry, construction industry, transport industry (car, aircraft, ship, train), for medical applications, for household and electrical appliances, vehicle parts, consumer articles, furniture, textiles. A further field of use is varnishes, paints and coatings.

For example, the compositions according to the invention can be used for marine applications (pontoons, planks, boats), auto applications (bumpers, batteries, trim parts, petrol tanks, cables, wires etc.), aircraft parts, railway parts, bicycle and motor cycle parts, space applications, such as e.g. satellite parts, housing parts for electrical appliances, such as computers, telephones, printers, audio and video systems, plugs, printed circuits, switches, lamp shades, refrigerators, coffee machines, vacuum cleaners, rotor blades for energy production, ventilators, foils for roof constructions, building foils, pipes, such as e.g. waste water pipes and gas pipes, connection parts, drainage systems, profiles, such as e.g. window profiles or cable channels, wood composites, furniture, flooring, covering plates, artificial grass, stadium seating, carpets, nets, ropes, furniture parts, mats, garden seats, outdoor boxes, containers and barrels.

The invention relates likewise to a method for the production of a previously described plastic material composition according to the invention in which the at least one organic oxyimide is incorporated before, after or at the same time as the at least one further flame retardant in the at least one plastic material, preferably the at least one thermoplastic polymer.

Incorporation of the above-described flame retardants and the additional additives in the plastic material is effected by normal processing methods, the polymer being melted and mixed with the flame retardants and additives, preferably by mixers, kneaders and extruders. As processing machines, extruders, such as e.g. single-screw extruders, twin-screw extruders, planet roller extruders, ring extruders, co-kneaders are preferred, which are preferably equipped with vacuum degassing. The processing can thereby be effected under air or possibly under inert gas conditions. Different flame retardants and additives can be added thereby separately or as a mixture, in the form of liquids, powders, granulates or compacted products or likewise in the form of master batches or concentrates which comprise for example 50-80% of the compositions according to the invention.

The invention likewise relates to a flame-retardant composition consisting of an organic oxyimide, comprising at least one structural element of the subsequently illustrated formula I,

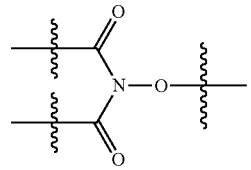

Formula I and a further flame retardant, the organic oxyimide being halogen-free.

The present invention is explained in more detail with reference to the subsequent embodiments without restricting the invention to the special parameters illustrated there.

Syntheses

Compound 1: N-hydroxyphthalimide, obtained from Aldrich

Compound 2: synthesis of N,N'-dihydroxypyromellitimide

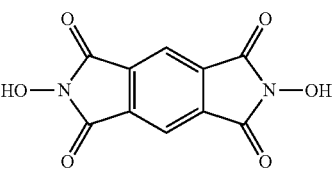 [SMILES: O=c1c2cc3c(=O)n(O)c(=O)c3cc2c(=O)n1O]

12.3 g (0.1773 mol, 2.2 eq.) hydroxylamine hydrochloride is dissolved in 100 ml of pyridine. 17.6 g (0.0807 mol, 1 eq.) of pyromellitic dianhydride is added to the solution. The reaction mixture is agitated for 2 h at 90° C. and subsequently for a further 12 h at room temperature. The precipitated residue is filtered off and washed with 5% hydrochloric acid and also with water. 12 g (60%) of a white product is obtained.

$^1$H-NMR (DMSO, 300 MHz) δ [ppm]=8.13 (s, 2H, CH), 11.15 (s, 2H, OH).

Compound 3: synthesis of N-hydroxynaphthalimide

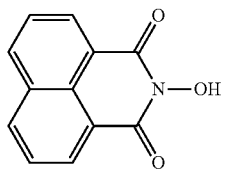 [SMILES: O=C1c2cccc3cccc(c23)C(=O)N1O]

4.9 g (0.0705 mol, 1.5 eq.) of hydroxylamine hydrochloride is dissolved in 60 ml of pyridine. 9.3 g (0.0469 mol, 1 eq.) of 1,8-naphthalic anhydride is added to the solution. The reaction mixture is agitated for 20 h at room temperature. The precipitated residue is filtered off and washed with 5% hydrochloric acid and also with water. 8 g (80%) of a white product is obtained.

$^1$H-NMR (DMSO, 300 MHz) δ [ppm]=7.87 (t, 2H, CH), 8.49 (dd, 4H, CH), 10.73 (s, 1H, OH).

Compound 4: synthesis of O,O'-terephthaloyl-bis-N,N'-phthalimide ester

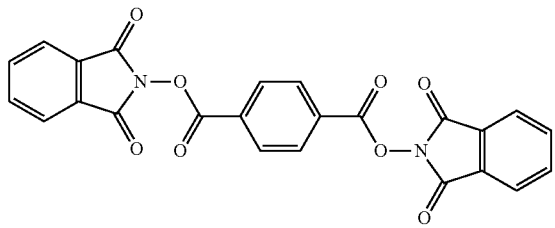 [SMILES: O=C(ON1C(=O)c2ccccc2C1=O)c1ccc(C(=O)ON2C(=O)c3ccccc3C2=O)cc1]

91 g of N-hydroxyphthalimide (0.5578 mol, 3 eq.) is dissolved in 200 ml of pyridine under a protective gas atmosphere. 38 g (0.1870 mol, 1 eq.) of terephthalic dichloride is added to the solution. The mixture is agitated for 2 h at 60° C. and subsequently for 12 h at room temperature. The white solid material is filtered off and washed with 5% hydrochloric acid and also with water. 76 g (89%) of white crystals is obtained.

$^1$H-NMR (DMSO, 300 MHz) δ [ppm]=8.05 (m, 8H, CH), 8.44 (s, 4H, CH).

Compound 5: synthesis of O,O'-succinyloyl-bis-N,N'-phthalimide ester

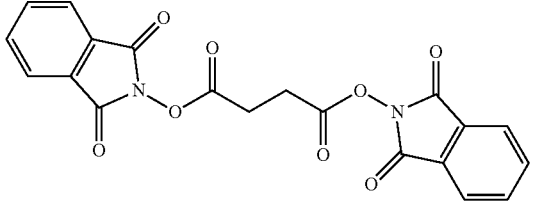 [SMILES: O=C(CCC(=O)ON1C(=O)c2ccccc2C1=O)ON1C(=O)c2ccccc2C1=O]

30 g (0.1840 mol, 3 eq.) of N-hydroxyphthalimide is dissolved in 180 ml of dry pyridine under a protective gas atmosphere. 6.75 ml (0.0613 mol, 1 eq.) of succinic dichloride is added in drops to the solution. The reaction mixture is agitated for 24 h at room temperature. The precipitated solid material is filtered off and washed with 5% hydrochloric acid and also with water. The purification is effected by recrystallisation in dichloromethane. 15 g (60%) of white crystals is obtained.

$^1$H-NMR (DMSO, 300 MHz) δ [ppm]=3.21 (s, 4H, CH$_2$), 7.96 (m, 8H, CH).

Compound 6: synthesis of O,O'-terephthaloyl-bis-N,N'-succinimide ester

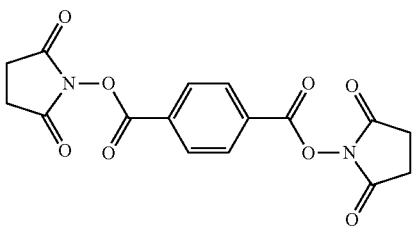 [SMILES: O=C(ON1C(=O)CCC1=O)c1ccc(C(=O)ON2C(=O)CCC2=O)cc1]

2.82 (0.0139 mol. 1 eq.) of terephthalic acid dichloride is suspended in a heated Schlenk flask under a nitrogen stream in 60 ml of dry pyridine. A second solution of 4.79 g (0.0417 mol, 3 eq.) of N-hydroxysuccinimide in 60 ml dry pyridine is added in drops to the suspension under a protective gas atmosphere and the reaction mixture is agitated for 24 h at room temperature. The precipitated residue is filtered off and washed with 5% hydrochloric acid (3×15 ml) and also with water. The obtained solid material is dried in a vacuum. 3.379 g (68%) of a white product is obtained.

$^1$H-NMR (DMSO, 300 MHz) δ [ppm]=2.92 (s, 8H, CH$_3$), 8.34 (s, 4H, CH).

Compound 7: synthesis of O,O',O''-trimesyloyl-tri-N,N',N''-phthalimide ester

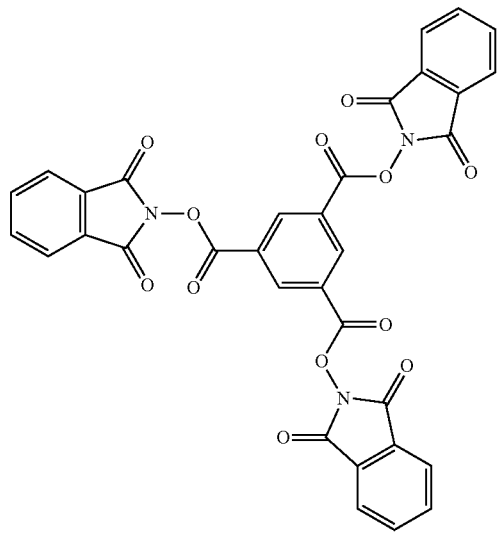 [SMILES: O=C(ON1C(=O)c2ccccc2C1=O)c1cc(C(=O)ON2C(=O)c3ccccc3C2=O)cc(C(=O)ON2C(=O)c3ccccc3C2=O)c1]

3.80 g (0.0232 mol, 3 eq.) of N-hydroxyphthalimide is dissolved with 2.1 ml (0.026 mol, 3.4 eq.) of pyridine in a heated Schlenk flask in the nitrogen stream in 83 ml of dry acetone and then cooled to 5° C. With agitation, a solution of 1.4 ml (0.0077 mol, 1 eq.) of trimesyltrichloride in 19 ml distilled acetone is added in drops with agitation. After completion of the addition, the mixture is agitated for 1 h at 5° C., subsequently the reaction mixture is agitated for 12 h at room temperature. The precipitated, white solid material is filtered off and washed with 5% hydrochloric acid and also with water. 3.9 g (78%) of a white product is obtained.

$^1$H-NMR (DMSO, 300 MHz) δ [ppm]=8.04 (m, 12H, CH), 9.09 (s, 3H, CH).

Compound 8: synthesis of O,O'-terephthaloyl-bis-N,N'-naphthalimide ester

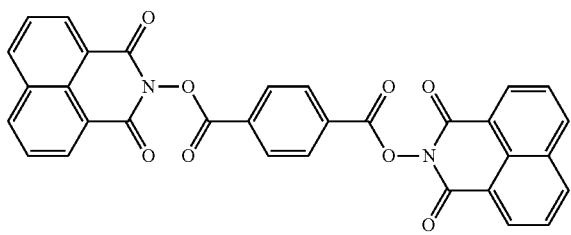 [SMILES: O=C(ON1C(=O)c2cccc3cccc(c23)C1=O)c1ccc(C(=O)ON2C(=O)c3cccc4cccc(c34)C2=O)cc1]

6.18 g (0.0290 mol, 2.5 eq.) of N-hydroxynaphthalimide is dissolved in a heated Schlenk flask in the nitrogen stream in 180 ml of dry pyridine at 45° C. Under a protective gas atmosphere, 2.3 g (0.0113 mol, 1 eq.) of terephthalic acid dichloride is added to the solution. The reaction mixture is agitated for 1 h at 45° C. and subsequently for a further 20 h at room temperature. The precipitated residue is filtered off and washed with 5% hydrochloric acid and also with water. 4.8 g (76%) of a white product is obtained.

$^1$H-NMR (ODCB, 300 MHz) δ [ppm]=7.41 (t, 4H, CH), 7.83 (d, 4H, CH), 8.12 (s, 4H, CH), 8.34 (d, 4H, CH).

EMBODIMENTS

The extrusions of the polypropylene samples (DOW 766-03) are effected at a temperature of 190° C. and a screw speed of rotation of 150 rpm on a DSM Micro 5cc, twin-screw extruder. The dwell time of the mixture in the bypass operation is 60 s. The desired mixture of polymer and additives (see subsequent table 1) is firstly mixed manually in a beaker glass and supplied in small portions to the microextruder. If the volume of the appliance is filled with melt, the material remains for another 60 s (dwell time) in the appliance and then is released.

The obtained plastic material strands are granulated (Pell-Tec SD 50 pure).

Test pieces for the fire test are produced from the granulate at a temperature of 220° C. and a pressure of 2 t using a hydraulic 10 t press (Werner & Pfleiderer). For this purpose, the granulate is filled into the compression mould and this is transferred into the already preheated press. At a pressure of 0.5 t, the granulate is firstly melted for 60 s. After expiry of the melt time, the pressure is increased to 2 t and kept constant for a further 3 min. Whilst maintaining the compression pressure, the mould is cooled to 60° C. and thereafter the test pieces are removed. The test pieces have, according to the standard, the following dimensions: 125× 12.5×1.5 mm.

The examples according to the invention and comparative examples contained in Table 1 were tested according to DIN EN 60695-11-10 and the burning times and classification according to the standard were obtained.

TABLE 1

Compositions in polypropylene and results of the fire test

| Example | Composition Flame retardant | Burning times as sum of the secondary burning times of 5 test pieces with 2 flame treatments [in seconds] | Classification according to DIN EN 60695-11-10 |
|---|---|---|---|
| Comparative example 1 (State of the art) | 8% diethylaluminium phosphinate + 2% distearyl hydroxylamine | 170 | Not classified |
| Comparative example 2 | 10% diethylaluminium phosphinate | >200 | Not classified |
| Example 1 according to the invention | 8% diethylaluminium phosphinate + 2% hydroxyphthalimide | 14 | V-2 |
| Example 2 according to the invention | 6% diethylaluminium phosphinate + 2% hydroxyphthalimide | 28 | V-2 |

Diethylaluminium phosphinate (Exolit OP 1230, manufacturer: Clariant)
Distearyl hydroxylamine, hydroxyphthalimide (obtained from Aldrich)

Surprisingly, the examples according to the invention have significantly curtailed burning times relative to the comparative examples at the same concentration.

TABLE 2

Compositions in polypropylene and results of the fire test

| Example according to the invention | Composition Flame retardant | Burning times as sum of the secondary burning times of 5 test pieces with 2 flame treatments [in seconds] | Classification according to DIN EN 60695-11-10 |
|---|---|---|---|
| Example 3 | 6% diethylaluminium phosphinate + 4% compound 2 | 27 | V-2 |
| Example 4 | 15% brominated polyacrylate + 5% compound 2 | 13 | V-2 |
| Example 5 | 2% phosphonate + 8% compound 2 | 10 | V-2 |
| Example 6 | 8% diethylaluminium phosphinate + 2% compound 3 | 27 | V-2 |
| Example 7 | 6% diethylaluminium phosphinate + 4% compound 3 | 25 | V-2 |
| Example 8 | 15% diethylaluminium phosphinate + 5% compound 4 | 15 | V-2 |
| Example 9 | 8% diethylaluminium phosphinate + 2% compound 4 | 33 | V-2 |
| Example 10 | 6% diethylaluminium phosphinate + 4% compound 4 | 33 | V-2 |
| Example 11 | 8% aluminium hypophosphite + 2% compound 4 | 34 | V-2 |
| Example 12 | 8% phosphonate + 2% compound 4 | 1 | V-0 |
| Example 13 | 6% phosphonate + 2% compound 4 | 15 | V-2 |
| Example 14 | 5% phosphonate + 5% compound 4 | 6 | V-2 |
| Example 15 | 6% phosphonate + 4% compound 4 | 0 | V-0 |
| Example 16 | 2% diethylaluminium phosphinate + 8% compound 5 | 16 | V-2 |
| Example 17 | 4% diethylaluminium phosphinate + 6% compound 5 | 26 | V-2 |
| Example 18 | 8% phosphonate + 2% compound 5 | 2 | V-2 |
| Example 19 | 6% phosphonate + 4% compound 5 | 0 | V-0 |
| Example 20 | 15% diethylaluminium phosphinate + 2% compound 6 | 35 | V-2 |
| Example 21 | 6% diethylaluminium phosphinate + 4% compound 6 | 29 | V-2 |
| Example 22 | 6% phosphonate + 4% compound 6 | 5 | V-2 |
| Example 23 | 6% phosphonate + 2% compound 6 | 10 | V-2 |
| Example 24 | 15% diethylaluminium phosphinate + 2% compound 7 | 17 | V-2 |
| Example 25 | 8% diethylaluminium phosphinate + 2% compound 7 | 9 | V-2 |
| Example 26 | 6% diethylaluminium phosphinate + 4% compound 7 | 11 | V-2 |
| Example 27 | 8% phosphonate + 2% compound 7 | 8 | V-0 |
| Example 28 | 6% phosphonate + 4% compound 7 | 4 | V-0 |
| Example 29 | 6% phosphonate + 2% compound 7 | 6 | V-0 |
| Example 30 | 5% phosphonate + 5% compound 7 | 5 | V-0 |
| Example 31 | 15% brominated polyacrylate + 5% compound 7 | 16 | V-2 |
| Example 32 | 15% diethylaluminium phosphinate + 2% compound 8 | 57 | V-2 |
| Example 33 | 8% phosphonate + 2% compound 8 | 0 | V-2 |
| Example 34 | 6% diethylaluminium phosphinate + 2% alkoxyamine + 2% compound 3 | 19 | V-2 |
| Example 35 | 6% diethylaluminium phosphinate + 2% disulphide + 2% compound 3 | 59 | V-2 |

Diethylaluminium phosphinate = Exolit OP 1230 of the company Clariant SE
Phosphonate = Aflammit PCO 900 of the company Thor GmbH
Aluminium hypophosphite = DP 111 of the company Velox
Brominated polyacrylate = FR 1025 of the company ICL-IP
Alkoxyamine = Flamestab NOR 116 of the company BASF SE
Disulphide = Hostanox SE 10 of the company Clariant SE

EXAMPLE 36

Analogously to examples 1-35 according to the invention, a thermoplastic polyurethane (Elastollan 1185A of the company BASF SE) was processed with 8% diethylaluminium phosphinate and 4% of compound 3 at 190° C. and compressed at 200° C. to form test pieces. The classification V-2 with a total burning duration (4 test pieces) of 1.3 seconds was obtained.

Analogously to examples 1-35, films made of polypropylene (Sabic 575 P) were produced and tested by means of the standard DIN 4102 B2, the results compiled in table 3 are obtained:

TABLE 3

Results of the flame-retardant polypropylene films

| Example | Composition Flame retardant | Maximum fire level [in mm] | Classification according to DIN 4102 B2 (passed/not passed) |
|---|---|---|---|
| Comparative example 3 | Without flame retardant | 150 | Not passed |
| Example 37 according to the invention | 4% compound 4 | 50 | Passed |
| Example 38 according to the invention | 2% compound 4 | 68 | Passed |
| Example 39 according to the invention | 0.4% compound 4 + 3.6% phosphonate | 88 | Passed |
| Example 40 according to the invention | 1% compound 4 + 2% phosphate | 75 | Passed |

Phosphonate = Aflammit PCO 900 of the company Thor GmbH
Phosphate = phosphoric acid, P,P'-[1,1'-biphenyl]-4,4'-diyl P,P,P'P'-tetraphenyl ester = ADK Stab FP 800 of the company Adeka

The invention claimed is:

1. A method for imparting flame retardancy to a plastic material such that it has a flame retardancy rating of V-2 or better and for synergistically enhancing the flame retardancy of a plastic material, the method comprising incorporating into the plastic material (i) an organic oxyimide comprising at least one structural element of Formula I

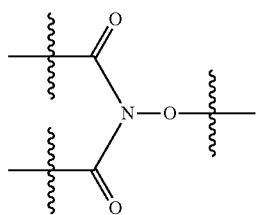

Formula I wherein the organic oxyimide is halogen-free and is selected from the group consisting of
  a) oxyimides comprising at least one structural element of Formula II,

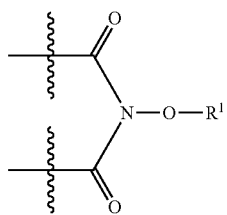

Formula II wherein $R^1$ is hydrogen or a substituted alkyl-, cycloalkyl-, aryl-, heteroaryl-, or acyl radical, and
  b) bridged oxyimides comprising at least one structural element of Formula III,

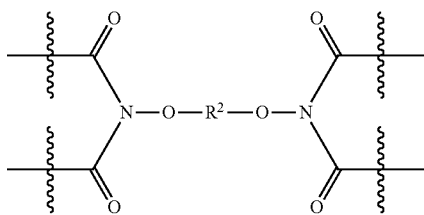

Formula III wherein $R^2$ is a substituted alkylene-, cycloalkylene-, arylene-, heteroarylene-, or bridging acyl radical, and
(ii) a flame retardant selected from the group consisting of (a), (b), (c), (d), and (e), and combinations thereof, wherein:
(a) is a phosphinate of the formula:

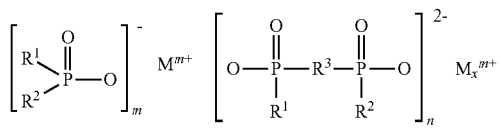

wherein $R^1$ and $R^2$ are identical or different and are selected from the group consisting of linear or branched $C_1$-$C_6$ alkyl and aryl; M is selected from the group consisting of Mg, Ca, Al, Sb, Sn, Ge, Ti, Fe, Zr, Ce, Bi, Sr, Mn, Li, Na, K, Zn, and a protonated nitrogen base; m =1-4; n=1-4; and x=1-4;

(b) is metal salt of hypophosphorous acid of the formula:

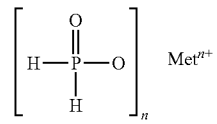

wherein Met is a metal selected from groups I, II, III, and IV of the periodic table of elements, and n is a number from 1 to 4 which corresponds to the charge of the corresponding metal ion Met;

(c) is a phosphonate or phosphonic acid diaryl ester of the formula:

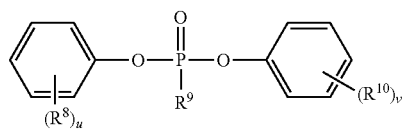

wherein $R^8$ and $R^{10}$ =H or alkyl, $R^9$ =$C_1$—$C_4$ alkyl, u=1-5, and v=1-5;

(d) is one or more of the following compounds:

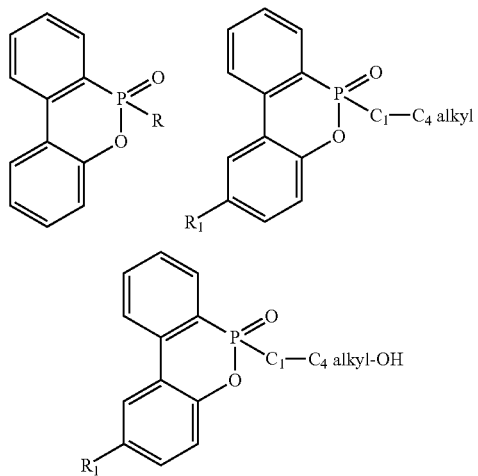

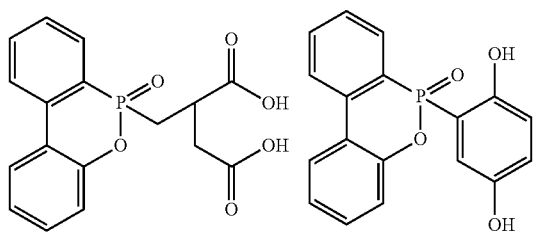

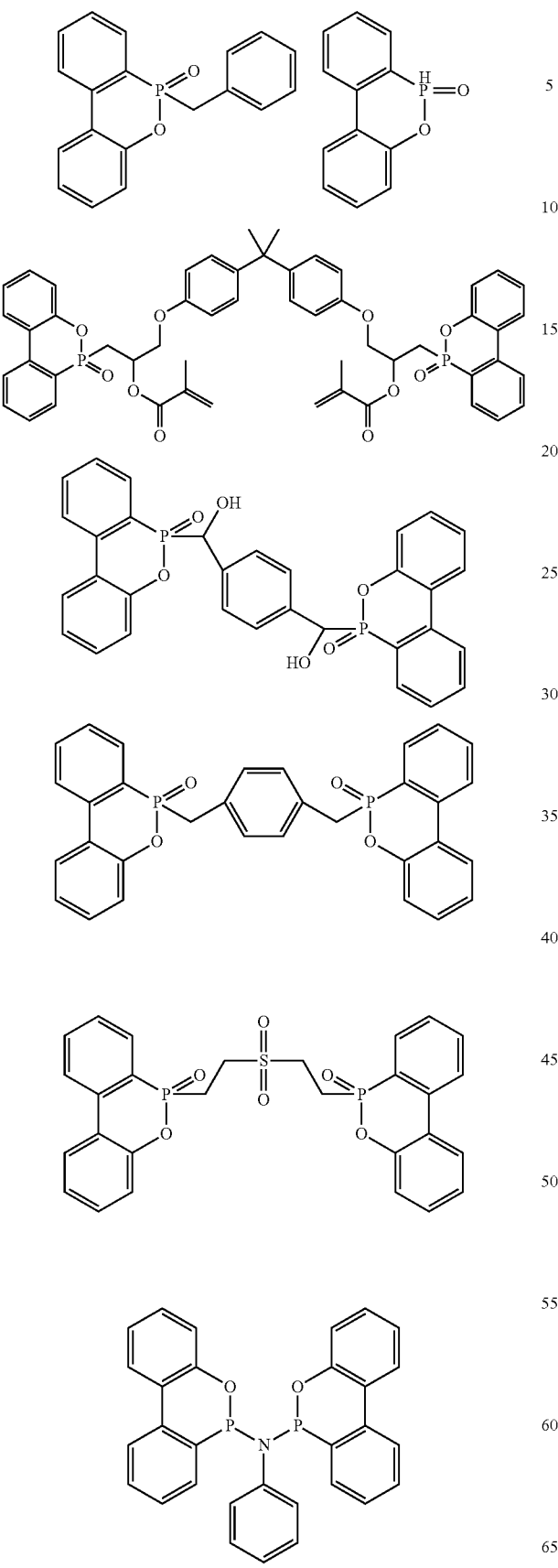
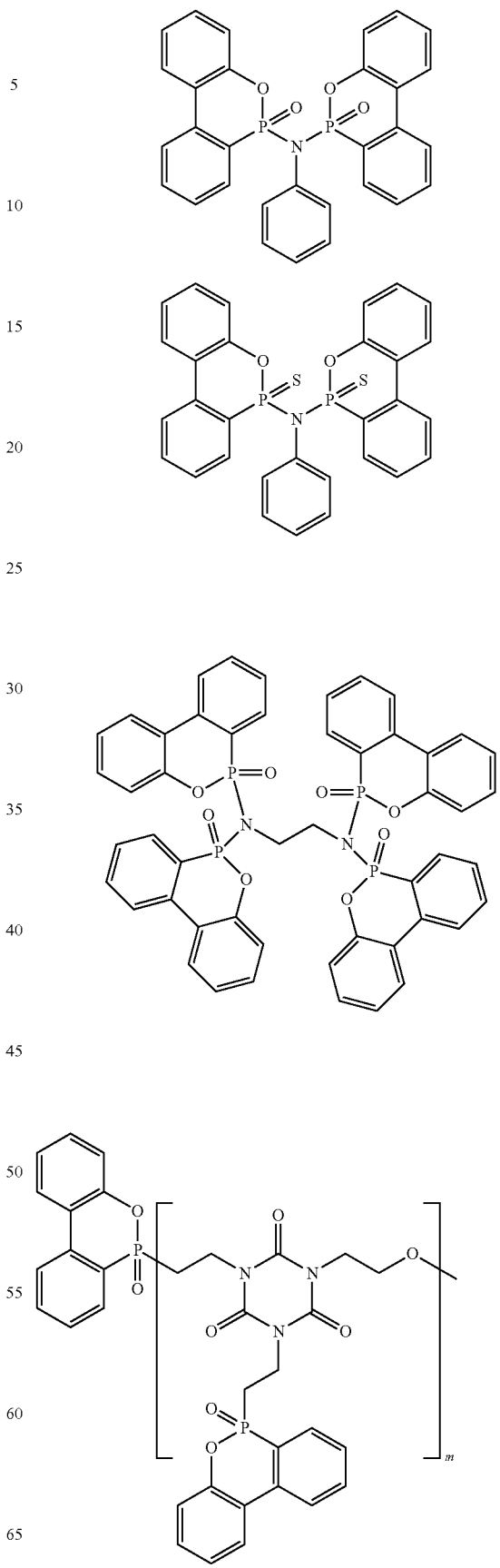

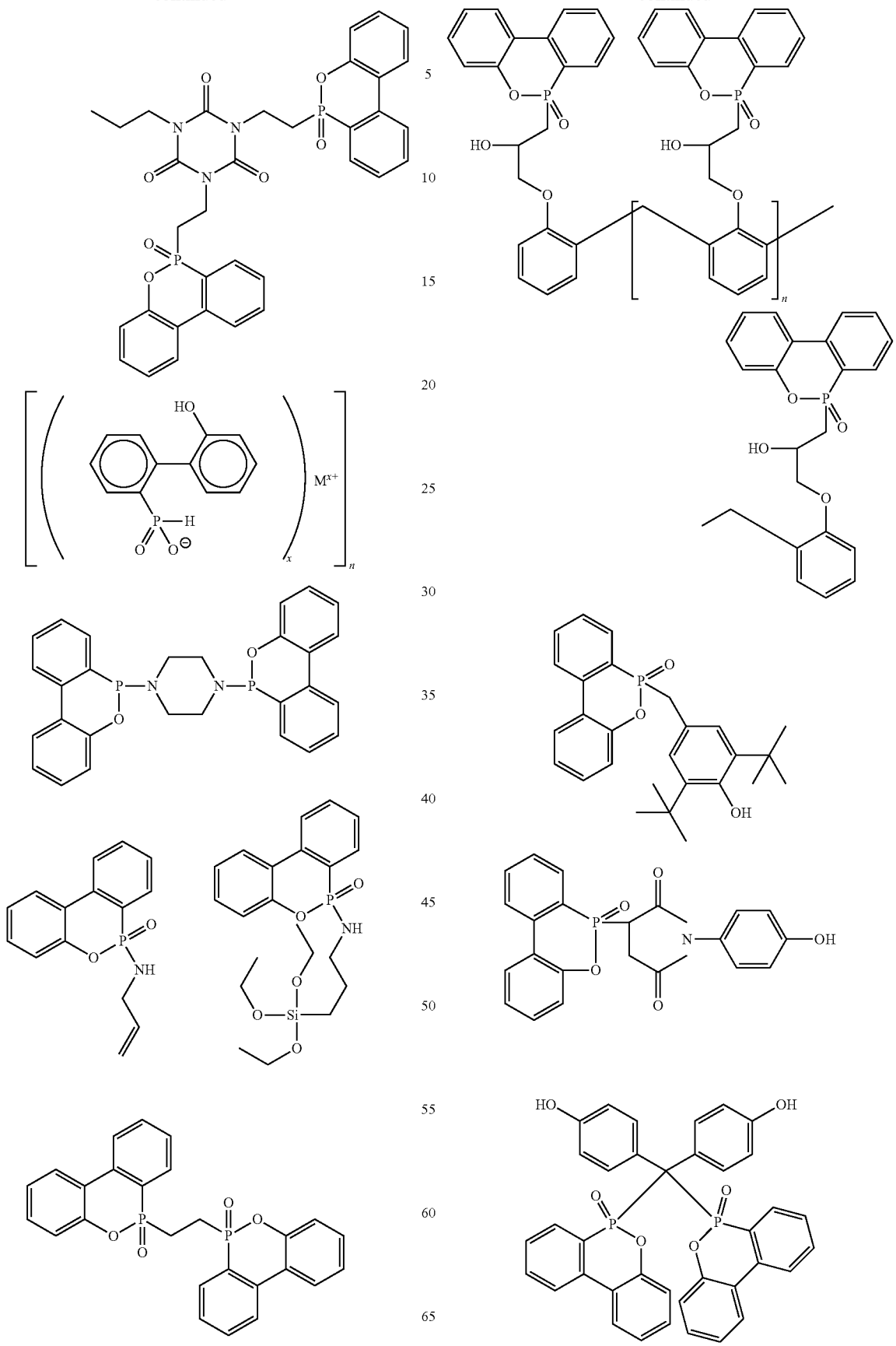

-continued

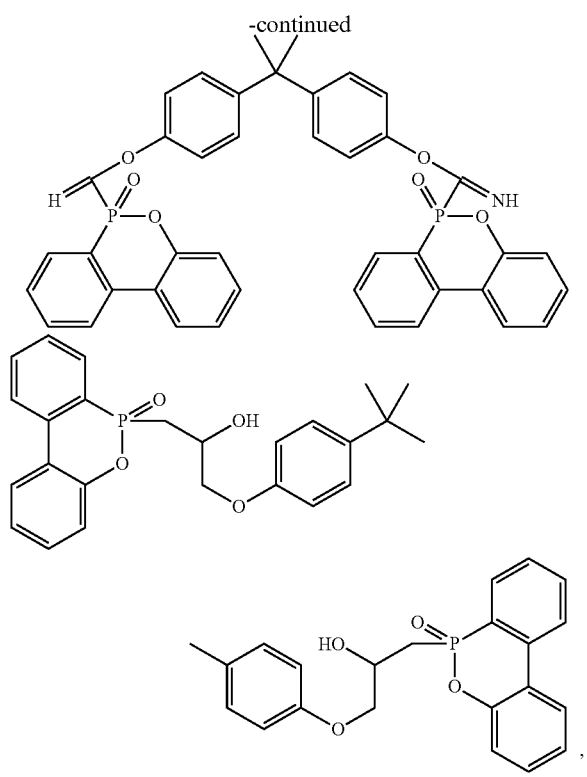

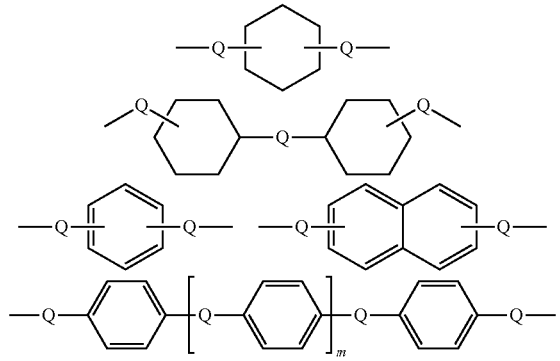

the cycloaliphatic or aromatic ring systems contained in the above groups being unsubstituted or substituted by one or more alkyl- and/or alkoxy groups, Q upon each occurrence, being the same or different and being selected from the group consisting of a chemical bond and radicals —$(CH_2)_n$— with n=1 to 18, —CH$(CH_3)$—, —$C(CH_3)_2$, —O—, —S—, —$SO_2$—, —NHCO—, —CO—, and m being 0 or 1 to 18.

3. The method according to claim 1, wherein the oxyimide has one of the following formulae,

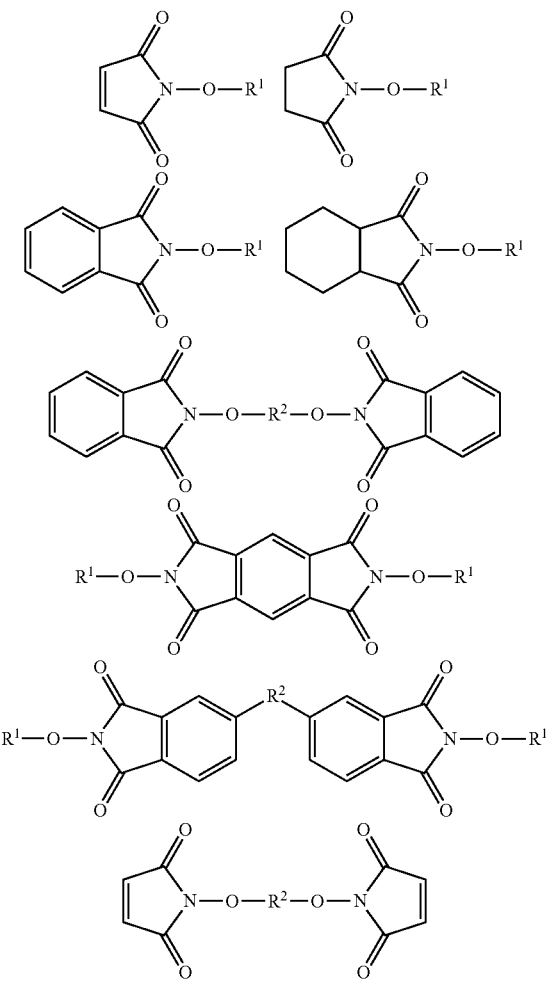

wherein M is a metal selected from the group consisting of second, third, twelfth and thirteenth group of the periodic table of the elements, x=2 or 3, n≥10, m =0-25, R=H, halogen or an aliphatic or aromatic radical with 1-32 C atoms and $R_1$=H or $C_1$-$C_6$ alkyl; and (e) is a cyclic phosphonate of the following formulae:

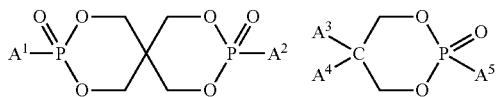

wherein $A^1$ and $A^2$, independently of each other, representing a substituted or unsubstituted, straight-chain or branched alkyl group with 1 to 4 carbon atoms, substituted or unsubstituted benzyl, substituted or unsubstituted phenyl, substituted or unsubstituted naphthyl, and $A^3$ and $A^4$, independently of each other, is methyl or ethyl and $A^5$ is a straight-chain or branched alkyl group with 1 to 4 carbon atoms or a phenyl- or benzyl group which can have respectively up to 3 methyl groups;

such that the plastic material, after incorporation of the organic oxyimide and the flame retardant or flame retardants, has a flame retardancy rating of V-2 or better, wherein the flame retardancy is measured according to DIN EN 60695-11-10, and wherein the flame retardancy is greater than the flame retardancy of the plastic material containing only a phosphorus-containing flame retardant, a nitrogen-containing flame retardant, or a sulphur-containing flame retardant, or combination thereof.

2. The method according to claim 1, wherein $R^2$ is selected from radicals of the group consisting of —$(CH_2)_n$— with n=1 to 18, —CH$(CH_3)$—, —$C(CH_3)_2$, —O—, —S—, —$SO_2$—, —NHCO—, —CO— and the following groups:

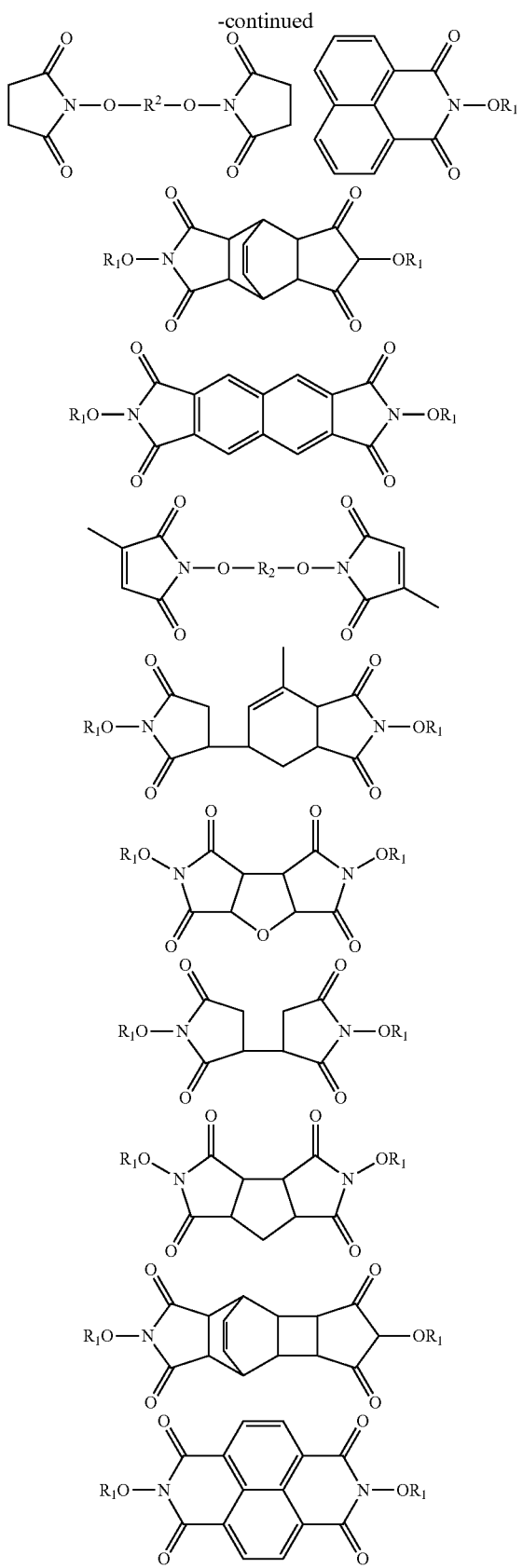

-continued respectively R¹ is hydrogen or a unsubstituted or substituted alkyl-, unsubstituted or substituted cycloalkyl-, unsubstituted or substituted aryl- or unsubstituted or substituted heteroaryl- or unsubstituted or substituted acyl radical, and R² is a substituted alkylene-, cycloalkylene-, arylene-, heteroarylene- or bridging acyl radical.

4. The method according to claim 3, wherein R¹=H or acyl.

5. The method according to claim 1, wherein the plastic materials are thermoplastic, elastomeric or duroplastic polymers.

6. The method according to claim 5, wherein the plastic materials are thermoplastic polymers selected from the group consisting of
   a) polymers made of olefins or diolefins and polyalkylene-carbon monoxide copolymers;
   b) polystyrene, polymethylstyrene, polyvinylnaphthalene, styrene-butadiene (SB), styrene-butadiene-styrene (SBS), styrene-ethylene-butylene-styrene (SEBS), styrene-ethylene-propylene-styrene, styrene-isoprene, styrene-isoprene-styrene (SIS), styrene-butadiene-acrylonitrile (ABS), styrene-acrylonitrile-acrylate (ASA), styrene-ethylene, styrene-maleic anhydride polymers including corresponding graft copolymers, graft copolymers made of methylmethacrylate, styrene-butadiene, styrene-butadiene-acrylonitrile (ABS), and methyl methacrylate-acrylonitrile-butadiene-styrene (MABS),
   c) halogen-containing polymers,
   d) polymers of unsaturated esters, polyacrylonitrile, polyacrylamides, and copolymers thereof,
   e) polymers made of unsaturated alcohols and derivatives thereof, polyacetals,
   g) polyphenylene oxides and blends with polystyrene or polyamides,
   h) polymers of cyclic ethers,
   i) polyurethanes made of hydroxy-terminated polyethers or polyesters and aromatic or aliphatic isocyanates,
   j) polyamides, partially or fully aromatic polyamides, and aromatic polyamides,
   k) polyimides, polyamideimides, polyetherimides, polyesterimides, poly(ether)ketones, polysulphones, polyethersulphones, polyarylsulphones, polyphenylenesulphide, polybenzimidazoles, and polyhydantoins,
   l) polyesters made of aliphatic or aromatic dicarboxylic acids and diols or made of hydroxycarboxylic acids,
   m) polycarbonates, polyester carbonates, and blends thereof,
   n) cellulose derivatives,
   o) non-thermoplastic or duroplastic plastic materials, and
   p) polyureas,
   q) mixtures, combinations or blends made of two or more of the previously mentioned polymers.

7. The method of claim 1, wherein the method comprises additionally incorporating into the plastic material a compound selected from the group consisting of triphenylphosphite, diphenylalkylphosphites, phenyldialkylphosphites, tri(nonylphenyl)phosphite, trilaurylphosphites, trioctadecylphosphite, distearylpentaerythritoldiphosphite, tris-(2,4-di-tert-butylphenyl)phosphite, diisodecylpentaerythritoldiphosphite, bis(2,4-di-tert-butylphenyl)pentaerythritoldiphosphite, bis(2,4-di-cumylphenyl)pentaerythritoldiphosphite, bis(2,6-di-tert-butyl-4-methylphenyl)pentaerythritoldiphosphite, diisodecyloxypentaerythritoldiphosphite, bis(2,4-di-tert-butyl-6-methylphenyl)pentaerythritoldiphosphite, bis(2,4,6-tris(tert-butylphenyl)pentaerythritoldiphosphite, tristearylsorbitoltriphosphite, tetrakis(2,4-di-tert-butylphenyl)-4,4-biphenylenediphosphonite, 6-isooctyloxy-2,4,8,10-tetratert-butyl-12H-dibenzo[d,g]-1,3,2-dioxaphocine, bis(2,4-di-tert-butyl-6-methylphenyomethylphosphite, bis(2,4-di-tert-butyl-6-methylphenyl)ethylphosphite, 6-fluoro-2,4,8,10-tetra-tert-butyl-12-methyl-dibenzo[d,g]-1,3,2-dioxaphosphocine, 2,2',2"-nitrilo[triethyltris(3,3',5,5'-tetra-tert-butyl-1,1'-biphenyl-2,2'-diyl)phosphite], 2-ethylhexyl (3,3', 5,5'-tetra-tert-butyl-1,1'-biphenyl-2,2'-diyl))phosphite, and 5-butyl-5-ethyl-2-(2,4,6-tri-tert-butylphenoxy)-1,3,2-dioxaphosphirane.

8. The method of claim 1, wherein the method comprises additionally incorporating into the plastic material one or more of the following compounds:

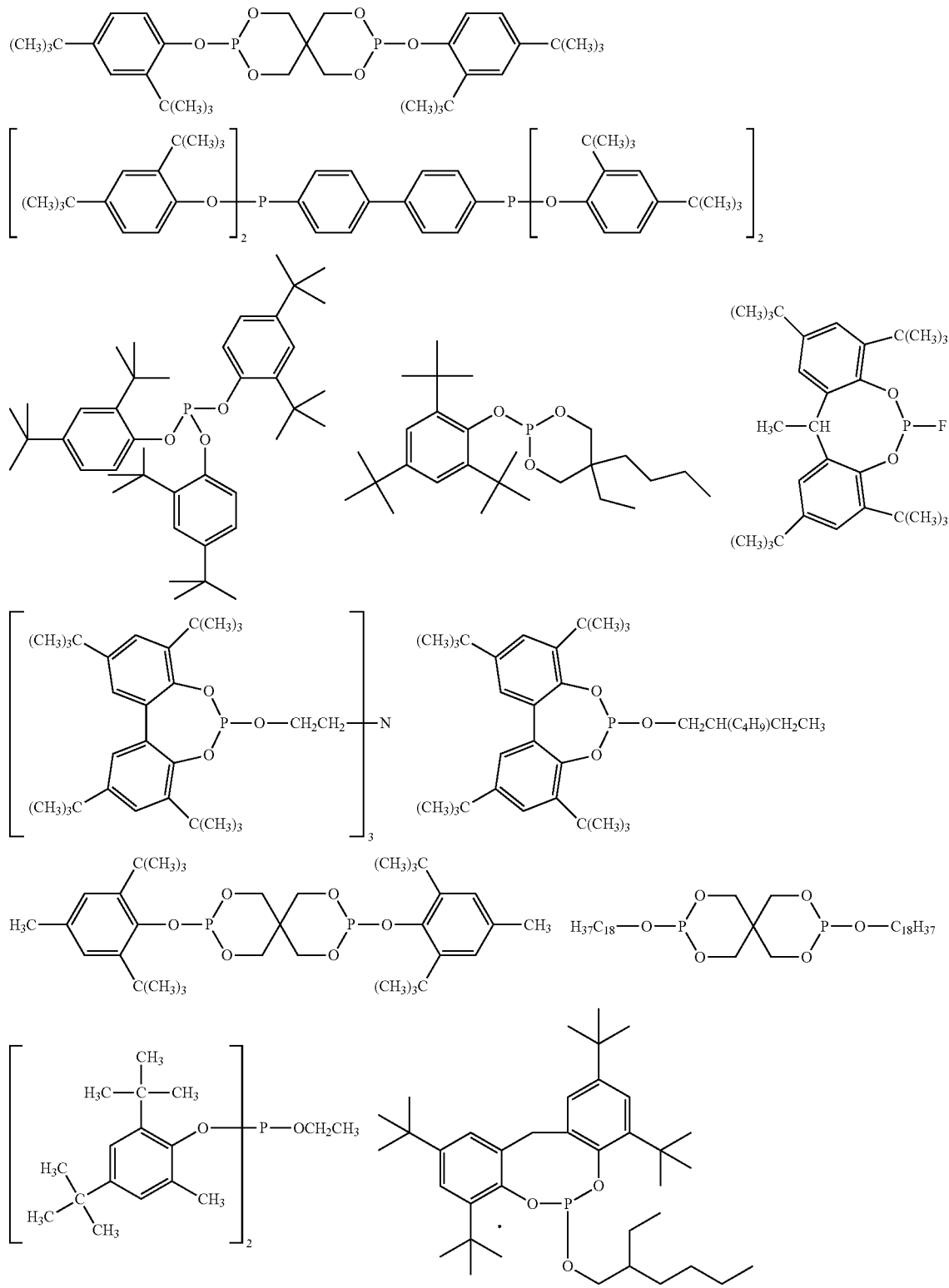

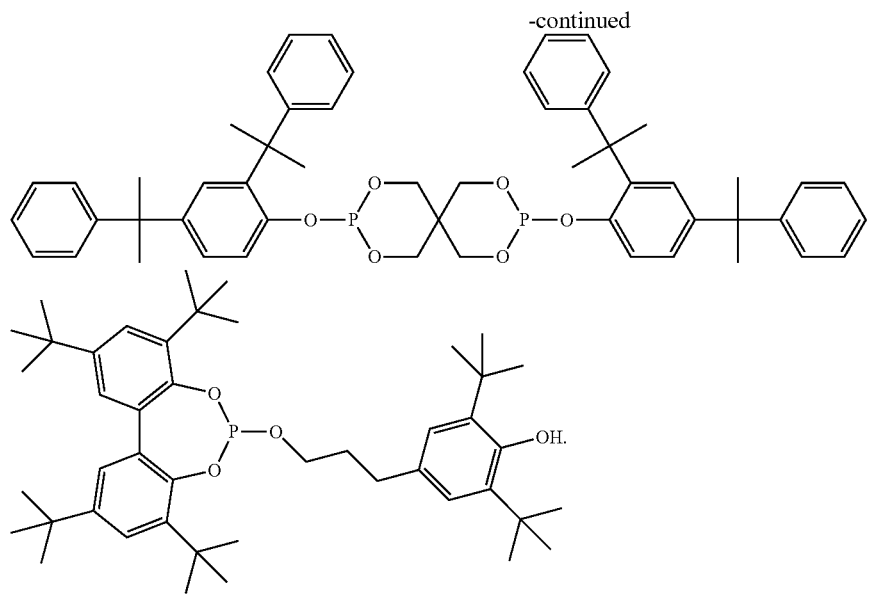
9. The method of claim 1, wherein the oxyimide is selected from the group consisting of:
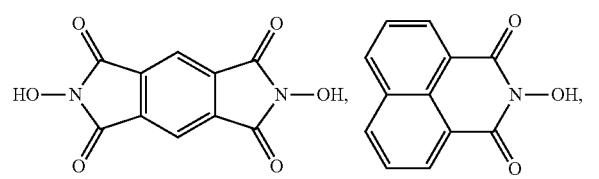
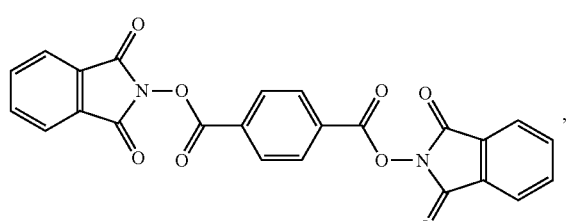
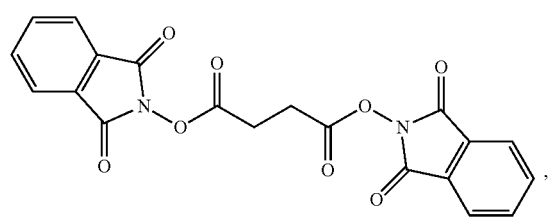
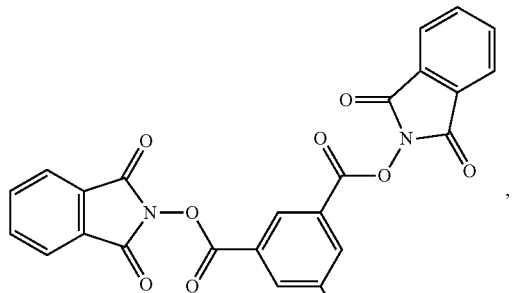
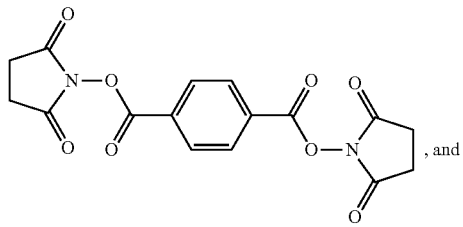
, and
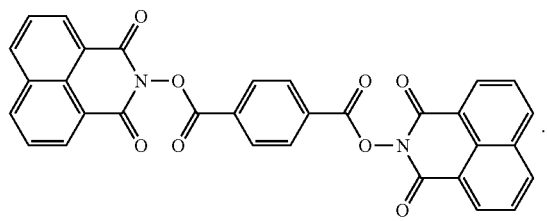
10. The method according to claim 5, wherein the plastic materials are thermoplastic polymers which are polyolefins.

11. The method of claim 1, wherein the plastic material after incorporation of the flame retardant contains 70 to 95 parts by weight of the plastic material, 2.5 to 15 parts by weight of the organic oxyimide, and 2.5 to 15 parts by weight of the flame retardant.

12. A method of synergistically enhancing the flame retardancy of a plastic material, the method comprising incorporating into the plastic material:
(i) an organic oxyimide N,N'-dihydroxypyromellitimide, N-hydroxynaphthalimide, O, O'-terephthaloyl-bis-N,N'-phthalimide ester, O, O'-succinyloyl-bis-N,N'-phthalimide ester, O, O'-terephthaloyl-bis-N,N'-succinimide ester, O, O', O''-trimesyloyl-tri-N, N', N''-phthalimide ester, and O, O'-terephthaloyl-bis-N, N'-naphthalimide ester and
(ii) a flame retardant selected from the group consisting of (a), (b), (c), (d), and (e), and combinations thereof, wherein:
(a) is a phosphinate of the formula:

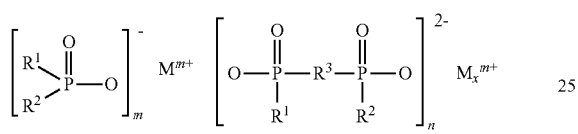

wherein $R^1$ and $R^2$ are identical or different and are selected from the group consisting of linear or branched $C_1$-$C_6$ alkyl and aryl; M is selected from the group consisting of Mg, Ca, Al, Sb, Sn, Ge, Ti, Fe, Zr, Ce, Bi, Sr, Mn, Li, Na, K, Zn, and a protonated nitrogen base; m=1-4; n=1-4; and x=1-4;
(b) is metal salt of hypophosphorous acid of the formula:

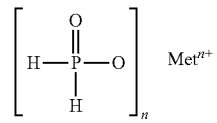

wherein Met is a metal selected from groups I, II, III, and IV of the periodic table of elements, and n is a number from 1 to 4 which corresponds to the charge of the corresponding metal ion Met;
(c) is a phosphonate or phosphonic acid diaryl ester of the formula:

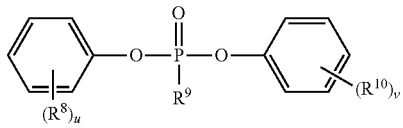

wherein $R^8$ and $R^{10}$ =H or alkyl, $R^9$ =$C_1$-$C_4$ alkyl, u=1-5, and v=1-5;
(d) is one or more of the following compounds:

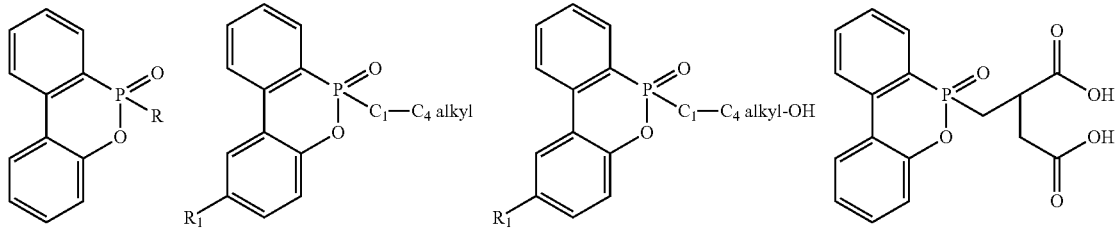

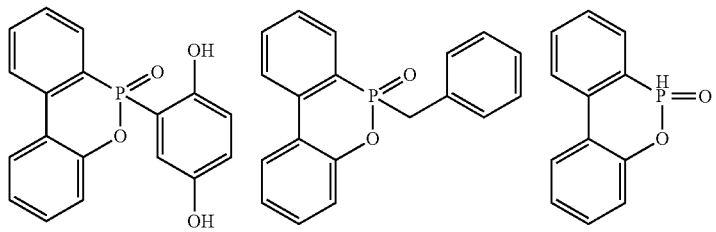

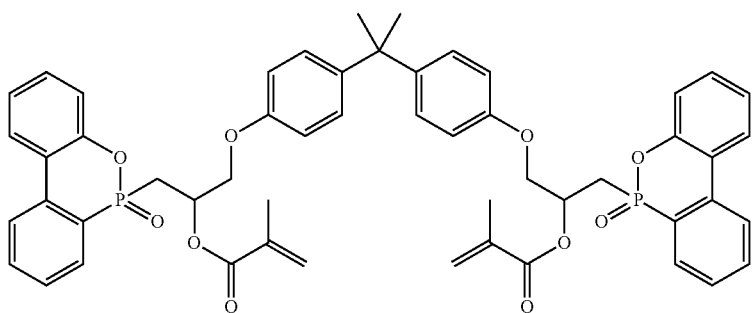

-continued
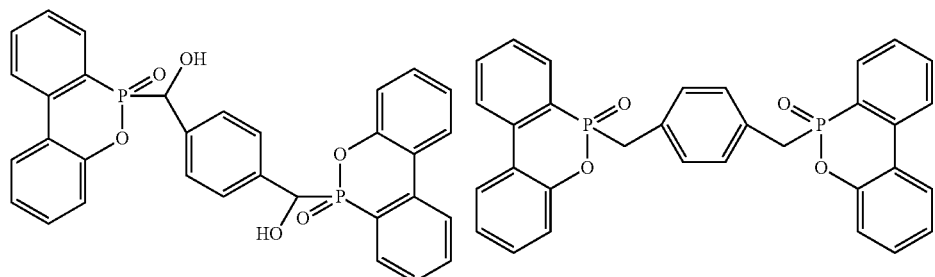
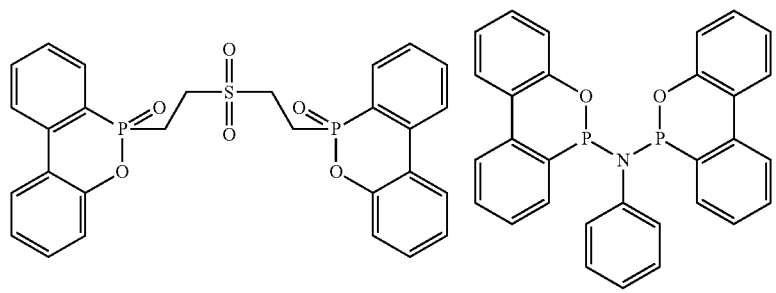
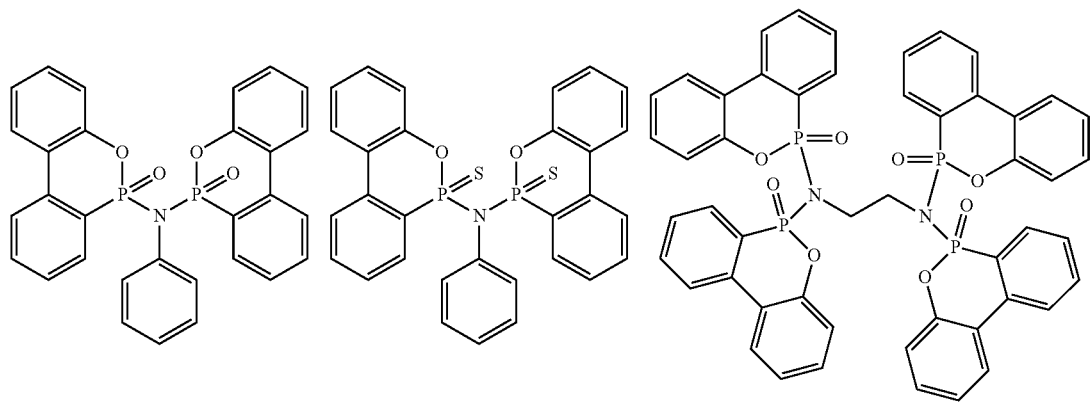
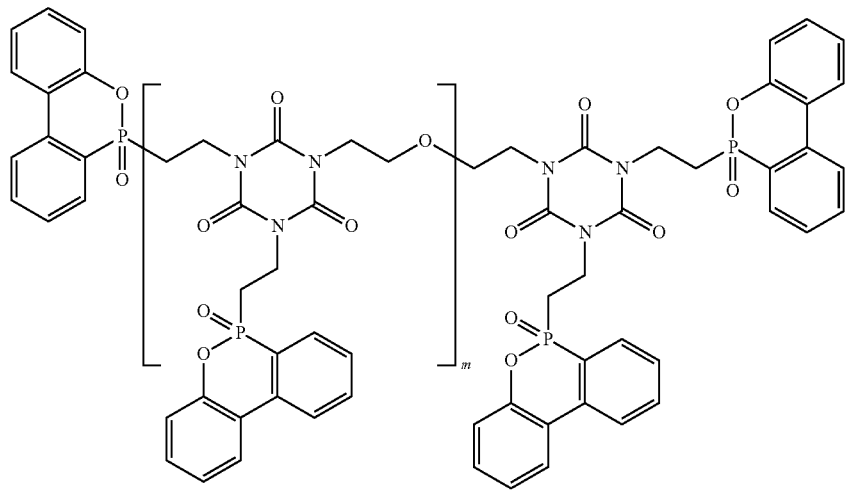

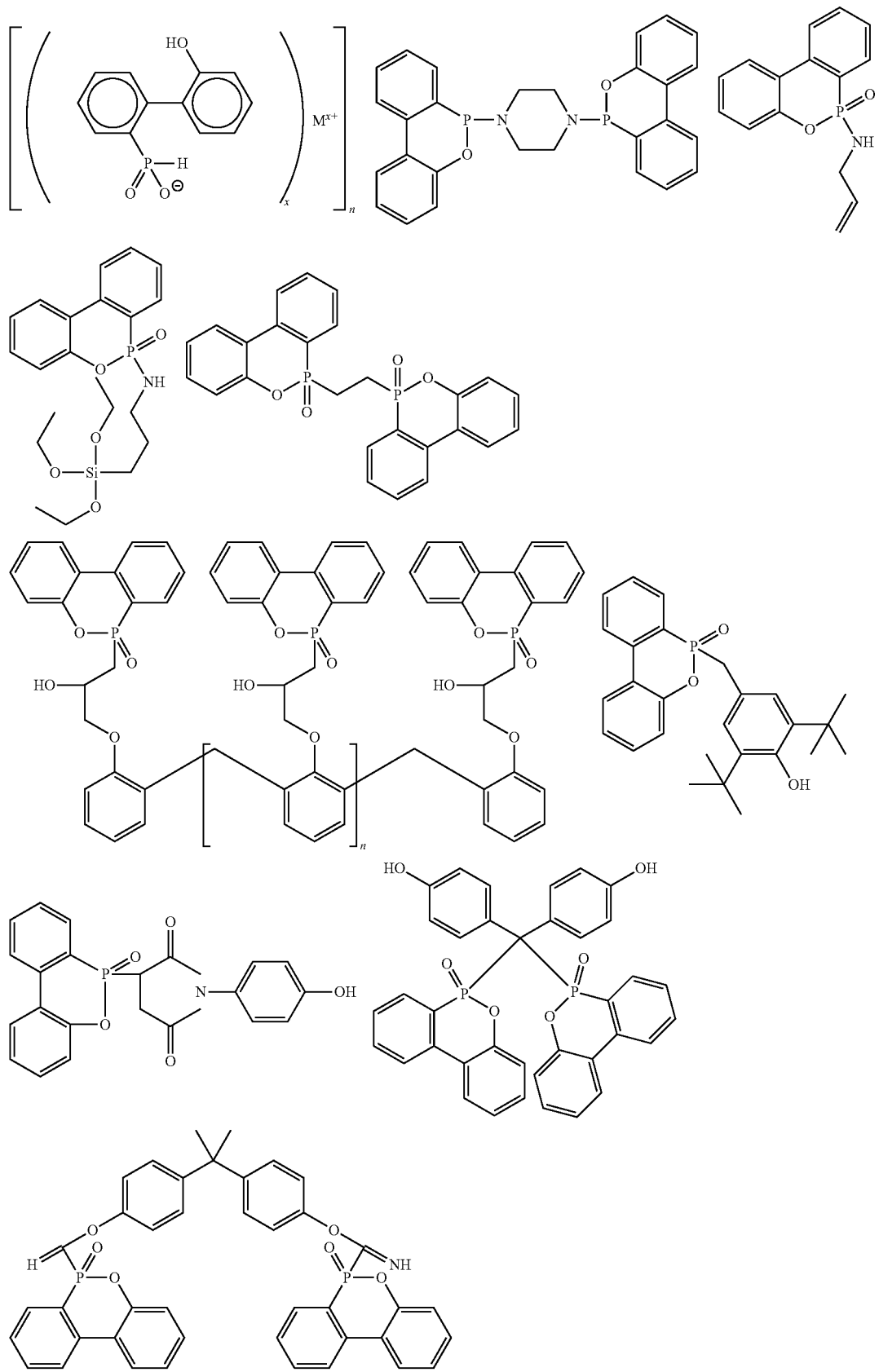

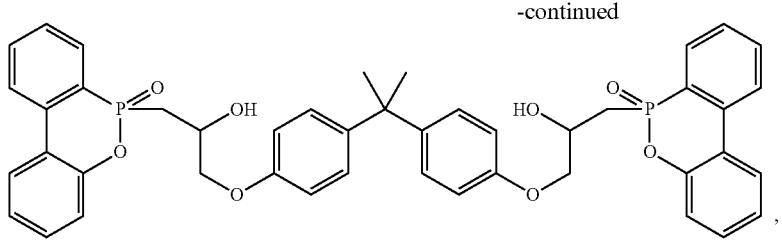

wherein M is a metal selected from the group consisting of second, third, twelfth and thirteenth group of the periodic table of the elements, x=2 or 3, n≥10, m =0-25, R=H, halogen or an aliphatic or aromatic radical with 1-32 C atoms and $R_1$=H or $C_1$-$C_6$ alkyl; and (e) is a cyclic phosphonate of the following formulae:

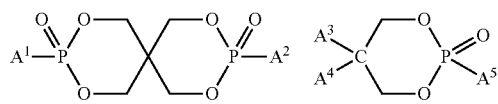

wherein $A^1$ and $A^2$, independently of each other, representing a substituted or unsubstituted, straight-chain or branched alkyl group with 1 to 4 carbon atoms, substituted or unsubstituted benzyl, substituted or unsubstituted phenyl, substituted or unsubstituted naphthyl, and $A^3$ and $A^4$, independently of each other, is methyl or ethyl and $A^5$ is a straight-chain or branched alkyl group with 1 to 4 carbon atoms or a phenyl- or benzyl group which can have respectively up to 3 methyl groups;

such that the plastic material, after incorporation of the organic oxyimide and the flame retardant or a combination of the flame retardants, has a flame retardancy which is greater than the flame retardancy of the plastic material containing the organic oxyimide only as the flame retardant and the flame retardancy of the plastic material containing only a phosphorus-containing flame retardant, a nitrogen-containing flame retardant, or a sulphurcontaining flame retardant, or combination thereof.

* * * * *